(12) United States Patent
Weitzman

(10) Patent No.: US 11,419,613 B2
(45) Date of Patent: Aug. 23, 2022

(54) TISSUE REMOVAL DEVICE

(71) Applicant: Carevature Medical Ltd., Tel-Aviv (IL)

(72) Inventor: Yoseph Weitzman, Tel-Aviv (IL)

(73) Assignee: CAREVATURE MEDICAL LTD., Tel-Aviv (IL)

( * ) Notice: Subject to any disclaimer, the term of this patent is extended or adjusted under 35 U.S.C. 154(b) by 932 days.

(21) Appl. No.: 14/427,408

(22) PCT Filed: Sep. 11, 2013

(86) PCT No.: PCT/IL2013/050769
§ 371 (c)(1),
(2) Date: Mar. 11, 2015

(87) PCT Pub. No.: WO2014/041540
PCT Pub. Date: Mar. 20, 2014

(65) Prior Publication Data
US 2015/0342619 A1 Dec. 3, 2015

Related U.S. Application Data

(60) Provisional application No. 61/699,315, filed on Sep. 11, 2012.

(51) Int. Cl.
*A61B 17/16* (2006.01)
*B65H 81/06* (2006.01)
*A61B 17/00* (2006.01)

(52) U.S. Cl.
CPC ...... *A61B 17/1631* (2013.01); *A61B 17/1659* (2013.01); *A61B 17/1671* (2013.01);
(Continued)

(58) Field of Classification Search
CPC ............ A61B 17/1615; A61B 17/1617; A61B 17/1622; A61B 17/1624; A61B 17/1628; A61B 17/1631
(Continued)

(56) References Cited

U.S. PATENT DOCUMENTS 2,000,997 A * 5/1935 Sharpe ...................... F16C 1/02
464/174
5,085,662 A 2/1992 Willard
(Continued)

FOREIGN PATENT DOCUMENTS

DE 10360076 4/2005
GB 751962 A 9/1956
(Continued)

OTHER PUBLICATIONS

OrthoMed, Inc. Spinal Rongeurs and Punches; uploaded on Apr. 18, 2013 (Apr. 18, 2013). Retrieved from: http://www.orthomedinc.com/wp-content/uploads/2013/04/18-O-Spinal-Rongeurs-and-Punches.pdf;20 pages.
(Continued)

*Primary Examiner* — Si Ming Ku
(74) *Attorney, Agent, or Firm* — Greenberg Traurig, LLP

(57) ABSTRACT

A device for cutting tissue including (a) an elongated shaft body defining a drive lumen, (b) a cutting head extending from a distal end of the elongated shaft body and being rotatable via a drive shaft disposed within the drive lumen, and (c) a retainer for keeping the cutting head attached to the shaft body if the cutting head becomes detached from the drive shaft or if the drive shaft breaks. A flexible drive shaft including (i) a core configured for resisting helixing, and (ii) at least one outer layer configured for transferring torque. A method of producing a flexible drive shaft including providing a core configured for resisting helixing, and wrapping
(Continued)

the core with at least one outer layer of wires configured for maintaining high torsional rigidity. Related apparatus and methods are also described.

22 Claims, 14 Drawing Sheets

(52) U.S. Cl.
CPC .......... *B65H 81/06* (2013.01); *A61B 17/1633* (2013.01); *A61B 17/1644* (2013.01); *A61B 2017/00526* (2013.01); *A61B 2017/1651* (2013.01)

(58) Field of Classification Search
USPC .......................................................... 606/80
See application file for complete search history.

(56) References Cited

U.S. PATENT DOCUMENTS

| | | | |
|---|---|---|---|
| 5,243,876 A * | 9/1993 | Mang | F16C 1/26 174/110 PM |
| 5,383,884 A | 1/1995 | Summers | |
| 5,395,188 A * | 3/1995 | Bailey | B23B 47/28 408/127 |
| 5,527,316 A | 6/1996 | Stone et al. | |
| 6,558,390 B2 | 5/2003 | Cragg | |
| 7,014,633 B2 | 3/2006 | Cragg | |
| 7,189,240 B1 | 3/2007 | Dekel | |
| 7,585,300 B2 | 9/2009 | Cha | |
| D606,654 S | 12/2009 | Tran et al. | |
| D611,146 S | 3/2010 | Way et al. | |
| 8,221,424 B2 | 7/2012 | Cha | |
| 2001/0021831 A1 | 9/2001 | Fleischhacker | |
| 2002/0090999 A1 | 7/2002 | Romano | |
| 2006/0089609 A1 | 4/2006 | Bleich et al. | |
| 2006/0135882 A1 | 6/2006 | Bleich | |
| 2006/0200155 A1 | 9/2006 | Harp | |
| 2006/0241648 A1 | 10/2006 | Bleich et al. | |
| 2008/0086034 A1 | 4/2008 | Schmitz et al. | |
| 2008/0183175 A1 | 7/2008 | Saal et al. | |
| 2008/0183192 A1 | 7/2008 | Saal et al. | |
| 2008/0221605 A1 | 9/2008 | Saal et al. | |
| 2009/0036936 A1 | 2/2009 | Solsberg et al. | |
| 2009/0143807 A1 | 6/2009 | Sand | |
| 2010/0082033 A1 | 4/2010 | Germain | |
| 2010/0211076 A1 | 8/2010 | Germain et al. | |
| 2010/0262147 A1 | 10/2010 | Siegal et al. | |
| 2010/0286695 A1 | 11/2010 | Hannani et al. | |
| 2010/0286698 A1 * | 11/2010 | Del Rio | A61B 17/1688 606/85 |
| 2010/0298832 A1 | 11/2010 | Lau et al. | |
| 2012/0209273 A1 * | 8/2012 | Zaretzka | A61B 17/32002 606/80 |

FOREIGN PATENT DOCUMENTS

| | | |
|---|---|---|
| NL | 1009471 | 12/1999 |
| WO | 91/12847 | 9/1991 |
| WO | 02/19928 | 3/2002 |
| WO | 2007/033052 | 3/2007 |
| WO | WO 2012/004766 | 1/2012 |
| WO | WO 2014/041540 | 3/2014 |

OTHER PUBLICATIONS

International Preliminary Report on Patentability dated Mar. 26, 2015 From the International Bureau of WIPO Re. Application No. PCT/IL2013/050769.
International Search Report and the Written Opinion dated Dec. 30, 2013 From the International Searching Authority Re. Application No. PCT/IL2013/050769.

* cited by examiner

TISSUE REMOVAL DEVICE

RELATED APPLICATIONS

This application is a National Phase of PCT Patent Application No. PCT/IL2013/050769 having International filing date of Sep. 11, 2013, which claims the benefit of priority under 35 USC § 119(e) of U.S. Provisional Patent Application No. 61/699,315 filed on Sep. 11, 2012. The contents of the above applications are all incorporated herein by reference as if fully set forth in their entirety.

FIELD AND BACKGROUND OF THE INVENTION

The present invention, in some embodiments thereof, relates to methods and devices for removing tissue from a body and, more particularly, but not exclusively, to methods and devices for minimally invasive tissue resection and drilling for optionally removing both hard and soft tissue from anatomically constrained sites such as within a spine or within joints.

Some pathological conditions in the human body can be caused by excess growth, displacement or anatomical mis-positioning of body tissue. For example, enlarged tissue such as a tumor can impinge upon an organ and adversely affect the function of that organ.

Pathological tissue may be removed via minimally invasive surgery (MIS) which may employ motorized or pneumatic/hydraulic cutters/drills or energy emitting devices such as RF ablation catheters, lasers and the like.

One specific condition which results from excess growth, displacement or anatomical mis-positioning of tissue is spinal stenosis.

In most cases of spinal stenosis, excess bone growth leads to narrowing of spaces in the spine joints which result in compression of spinal cord and/or nerve roots. This can lead to pain or numbness in the legs and/or arms depending on the location of the affected nerve within the spine joints (e.g. cervical, thoracic, lumbar regions).

A variety of treatment approaches can be used to alleviate or minimize the effects of spinal stenosis. One such treatment approach is a laminectomy, which involves removing the lamina portion from the pathologic region and thereby relieving the pressure on the compressed nerves.

PCT Published patent application WO 2012/004766 of Yoseph Weitzman describes an elongate tool with a cutting end. In some embodiments the end is bendable. Optionally, the end is bendable between two cutting edges. Optionally or alternatively, the end includes both a forward cutting edge and a side cutting edge. The tool may be sized for hand-held use, with control from outside the body, for treating a spinal stenosis.

Additional background art includes:
U.S. Pat. No. 5,527,316;
U.S. Pat. No. 6,558,390;
U.S. Pat. No. 7,014,633;
U.S. Pat. No. 7,189,240;
U.S. Patent Application Publication No. 2006/0200155;
U.S. Patent Application Publication No. 2006/0135882;
U.S. Patent Application Publication No. 2006/0089609;
U.S. Patent Application Publication No. 2006/0241648;
U.S. Patent Application Publication No. 2008/0086034;
U.S. Patent Application Publication No. 2009/0036936;
U.S. Patent Application Publication No. 2009/0143807;
U.S. Patent Application Publication No. 2010/0262147;
U.S. Patent Application Publication No. 2008/0183175;
U.S. Patent Application Publication No. 2008/0183192;
U.S. Patent Application Publication No. 2008/0221605;
U.S. Patent Application Publication No. 2010/0082033;
U.S. Patent Application Publication No. 2010/0211076;
U.S. Patent Application Publication No. 2006/0200155;
U.S. Patent Application Publication No. 2010/0286695;
U.S. Patent Application Publication No. 2010/0298832;
U.S. Design Pat. No. D611146;
U.S. Design Pat. No. D606654;
German Patent No. DE 103 60 076; and
Netherland Patent No. NL 1009471.

The disclosures of all references mentioned above and throughout the present specification, as well as the disclosures of all references mentioned in those references, are hereby incorporated herein by reference.

SUMMARY OF THE INVENTION

In some embodiments of the invention, a surgical device for cutting tissue is provided which includes an elongated shaft body defining a drive lumen and a rotating cutting head extending from a distal end of the elongated shaft body.

In some embodiments, the cutting head is designed to rotate at high rotational rates, and at high torque, for example for cutting bone.

In some embodiments, the elongated shaft and the cutting head are designed for use in narrow spaces, and are narrow themselves.

In some embodiments, the elongated shaft and a drive shaft are designed to operate when bent at an angle and/or flexible and bendable.

Being narrow, and sometimes operating bent at an angle, the drive shaft or a connection of the drive shaft to the rotating cutting head may break under load.

In some embodiments, a retainer is used, for keeping the cutting head attached to the shaft body should the cutting head becomes detached from the drive shaft or should the drive shaft break.

In some embodiments, the flexible shaft is built according to a design which can reduce breaking when operating under some of the operating conditions described herein.

According to an aspect of some embodiments of the present invention there is provided a device for cutting tissue including (a) an elongated shaft body defining a drive lumen, (b) a cutting head extending from a distal end of the elongated shaft body and being rotatable via a drive shaft disposed within the drive lumen, and (c) a retainer for keeping the cutting head attached to the shaft body if the cutting head becomes detached from the drive shaft or if the drive shaft breaks.

According to some embodiments of the invention, the retainer does not rotate.

According to some embodiments of the invention, the elongated shaft body includes a curved distal portion and the cutting head extends from a distal end of the curved distal portion.

According to some embodiments of the invention, the retainer prevents lateral movement, relative to axis of the elongated shaft body, of the cutting head if the cutting head becomes detached from the drive shaft or if the drive shaft breaks.

According to some embodiments of the invention, further including a shield extending around at least a portion of the cutting head. According to some embodiments of the invention, the retainer is attached to the shield.

According to some embodiments of the invention, the retainer includes a sleeve surrounding a portion of the cutting head and attached to the elongated shaft body.

According to some embodiments of the invention, the cutting head includes a groove and the retainer includes a component configured for engaging the groove for retaining the cutting head within the distal portion of the elongated device body if the cutting head becomes detached from the drive shaft or if the drive shaft breaks.

According to some embodiments of the invention, the component configured for engaging the groove includes a tenon. According to some embodiments of the invention, the component configured for engaging the groove includes a pin. According to some embodiments of the invention, the component configured for engaging the groove includes a snap.

According to some embodiments of the invention, the component configured for engaging the groove is further configured to have low friction with the cutting head.

According to some embodiments of the invention, the cutting head includes two parts, a first part of the cutting head is connected to the drive shaft, and a second part of the cutting head is connected to the first part, wherein the second part is configured for cutting tissue.

According to some embodiments of the invention, the first part of the cutting head is screwably attached to the second part of the cutting head. According to some embodiments of the invention, the first part of the cutting head is attached to the second part of the cutting head by a tenon.

According to some embodiments of the invention, the cutting head is cylindrical in shape with a circumferential surface configured for cutting of tissue. According to some embodiments of the invention, the cutting head is conical in shape with a distal end portion in diameter then a proximal portion. According to some embodiments of the invention, at least part of the cutting head includes a diamond coating. According to some embodiments of the invention, a distal tip of the cutting head is configured for tissue drilling.

According to some embodiments of the invention, the cutting head includes a groove and the retaining mechanism includes a drive shaft sleeve crimped onto the groove for retaining the cutting head within the distal portion of the elongated device body if the drive shaft becomes detached from the cutting head.

According to some embodiments of the invention, the cutting head is configured to be detachable from the drive shaft using hand tools.

According to some embodiments of the invention, the drive shaft includes a wire cable including a plurality of layers, the wire cable being configured for torsional rigidity and low bending rigidity.

According to some embodiments of the invention, the wire cable includes (i) a core configured for resisting helixing, and (ii) at least one outer layer configured for maintaining high torsional rigidity.

According to some embodiments of the invention, the core includes a braid including a plurality of wires. According to some embodiments of the invention, the core includes a plurality of layers including braided wires.

According to some embodiments of the invention, the at least one outer layer includes a plurality of outer layers, and wherein each layer of the plurality of outer layers is configured to have mechanical properties in a direction opposite to the direction of the adjacent outer layer.

According to some embodiments of the invention, the at least one outer layer includes a plurality of outer layers, and wherein each layer of the plurality of outer layers includes a layer of wires wound, relative to the core, in a direction opposite to the direction of an adjacent outer layer.

According to some embodiments of the invention, the wire cable is configured to operate when permanently bent at an angle in a range between 90 and 160 degrees. According to some embodiments of the invention, the wire cable is configured to operate when temporarily bent at an angle in a range between 90 and 160 degrees.

According to some embodiments of the invention, the wire cable is configured to provide bidirectional rotation.

According to some embodiments of the invention, configured to support a rotational speed of up to 40,000 rpm. According to some embodiments of the invention, the wire cable is configured to support a torque of up to 5 Ncm.

According to some embodiments of the invention, the wire cable is configured to support a rotational speed of up to 40,000 rpm when bent at an angle in a range between 90 and 160 degrees.

According to some embodiments of the invention, the drive shaft includes a tube crimped over the wire cable.

According to an aspect of some embodiments of the present invention there is provided a method of cutting tissue including using a device constructed according to claim 1, positioning the cutting head of the device against tissue, and operating the device to cut the tissue.

According to some embodiments of the invention, further including having the drive shaft break, and keeping the cutting head attached to the shaft body.

According to some embodiments of the invention, further including having the cutting head become detached from the drive shaft, and keeping the cutting head attached to the shaft body.

According to some embodiments of the invention, the method is applied for treating spinal stenosis. According to some embodiments of the invention, the method is applied for performing at least one of the procedures selected from a group including laminotomy, laminectomy, foraminotomy, discectomy, and facetectomy.

According to an aspect of some embodiments of the present invention there is provided a flexible drive shaft including (i) a core configured for resisting helixing, and (ii) at least one outer layer configured for transferring torque.

According to some embodiments of the invention, the at least one outer layer includes a plurality of outer layers, and at least all of the outer layers are configured for transferring torque.

According to some embodiments of the invention, the core includes a plurality of wires. According to some embodiments of the invention, the core includes a braid including a plurality of wires. According to some embodiments of the invention, the core includes a plurality of layers including braided wires. According to some embodiments of the invention, the core includes a nylon rod.

According to some embodiments of the invention, the at least one outer layer includes a plurality of outer layers, and wherein each layer of the plurality of outer layers includes a layer of wires wound, relative to the core, in a direction opposite to the direction of an adjacent outer layer.

According to an aspect of some embodiments of the present invention there is provided a method of producing a flexible drive shaft including providing a core configured for resisting helixing, and wrapping the core with at least one outer layer of wires configured for maintaining high torsional rigidity.

According to some embodiments of the invention, the at least one outer layer includes a plurality of outer layers, and wherein each layer of the plurality of outer layers includes a layer of wires wound, relative to the core, in a direction opposite to the direction of an adjacent outer layer.

According to one aspect of the present invention there is provided a device for cutting and removing tissue comprising: (a) an elongated device body having a curved distal portion; (b) a cutting head extending from a distal end of the curved distal portion and being rotatable via a drive shaft disposed within a drive lumen of the elongated shaft; and (c) a mechanism for retaining the cutting head when detached from the drive shaft.

According to further features in some embodiments of the invention described below, the cutting head may be substantially cylindrical in shape with circumferential surface configured for cutting of tissue.

According to still further features in some described embodiments the cutting head may be a substantially conical cutting head with a distal end smaller in diameter than a proximal end.

According to still further features in some described embodiments the device further comprises a shield positionable over a portion of the circumferential surface.

According to still further features in some described embodiments a distal tip of the cutting head may be configured for tissue drilling.

According to still further features in some described embodiments the shield may be rotatable around the cutting head.

According to still further features in some described embodiments the cutting head may be configured with a groove and the mechanism includes an element capable of engaging the groove for retaining the cutting head within the distal portion of the elongated device body when the drive shaft is detached from the cutting head.

According to still further features in some described embodiments an angle between the curved distal portion and a linear portion of the elongated device body may be, for example, between 90 to 160 degrees.

According to still further features in some described embodiments the angle may be, for example, 105 degrees.

According to still further features in some described embodiments a length of the cutting head may be, for example, between 3 to 30 mm.

According to still further features in some described embodiments a length of the cutting head may be, for example, between 3 and 15 mm.

According to still further features in some described embodiments a length of the elongated device body may be, for example, between 10 to 500 mm.

According to still further features in some described embodiments a length of the elongated device body may be, for example, between 150 to 200 mm.

According to still further features in some described embodiments the device further comprises an irrigation lumen within the elongated device body.

According to still further features in some described embodiments the drive shaft includes a multi-layer wire cable configured for high torsional rigidity and low bending rigidity.

According to still further features in some described embodiments the multi-layer wire cable includes: (i) inner layers configured for maintaining high structural integrity and (ii) outer layers configured for maintaining high torsional rigidity (iii) each layer may be configured to have mechanical properties in a direction opposite to the direction of the adjacent layer.

According to still further features in some described embodiments the multi-layer wire cable may be capable of supporting an optionally bidirectional rotational speed of up to, for example, 40,000 rpm and a torque of up to, for example, 5 Ncm.

According to still further features in some described embodiments a proximal end of the elongated device body includes a seal for sealing the irrigation lumen, even over a shaft rotating at high speed.

According to still further features in some described embodiments the seal may be composed of a temperature resistant material having a Shore durometer value of, for example, 50 A or less.

According to still further features in some described embodiments the temperature resistant material may be silicon rubber, self-lubricating silicon rubber or self-lubricating silicon rubber including silicon oil having a temperature independent viscosity.

According to still further features in some described embodiments a proximal end of the elongated device body includes a mechanism for forcing flow of fluid within the irrigation fluid under rotation of the drive shaft.

According to still further features in some described embodiments the drive shaft includes a tube crimped over the multi-layer wire cable.

According to another aspect of the present invention there is provided a method of cutting tissue in a procedure such as laminotomy comprising positioning the cutting head of the device described herein against the tissue and operating the device to thereby cut the tissue, optionally while removing the debris of the cut tissue out of the surgical site.

Some embodiments of the present invention successfully address the shortcomings of the presently known configurations by providing a device for cutting tissue which may be configured for minimizing damage to non-treated tissue.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of some embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of some embodiments of the invention, the description taken with the drawings making apparent to those skilled in the art how embodiments of the invention may be embodied in practice.

In the drawings.

DESCRIPTION OF SPECIFIC EMBODIMENTS OF THE INVENTION

Figure 1:
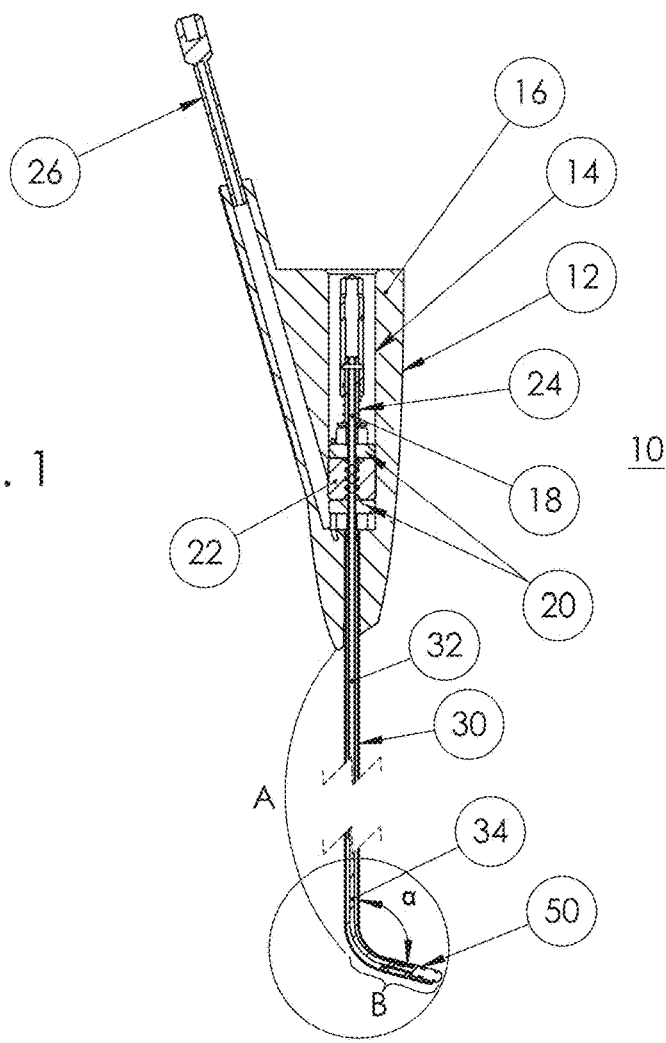
FIG. 1 is a side cutaway view of a device constructed as an example embodiment of the invention showing a handle, an elongated shaft and a cutting head.

The present invention, in some embodiments thereof, relates to methods and devices for removing tissue from a body and, more particularly, but not exclusively, to methods and devices for minimally invasive tissue resection and drilling for optionally removing both hard and soft tissue from anatomically constrained sites within the spine or other joint, e.g. shoulder, hip, knee, and so on.

Some embodiments of the present invention are of a surgical device which can be used to resect pathological tissue such as that associated with spinal stenosis.

The principles and operation of some embodiments of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

In a previously filed patent application (WO 2012/004766), the present inventor described a tissue removal device with an elongated flexible shaft and a shielded tissue cutting head. Embodiments of the present invention may be used to enhance features of the above-mentioned device.

For example, cutting and drilling devices may suffer from possible mechanical failures of the cutting head, possible detachment of the cutting head from the device, release of mechanical parts from the device into the body during surgery, and other malfunctions, which can result in tissue trauma and a body's reactions to foreign object(s).

The present invention, in some embodiments thereof, improves on prior art designs by including a mechanism for preventing a cutting head failure from detaching from the device following events such as detaching of the drive shaft from the cutting head or breakage of the drive shaft.

The present invention, in some embodiments thereof, improves on prior art designs by including a mechanism for preventing a cutting head from causing wobble or lateral straying of the cutting head from alignment following events such as detaching of the drive shaft from the cutting head or breakage of the drive shaft.

In some embodiments, a mechanism provides both of the above improvements. In some embodiments, one mechanism prevents detaching of the cutting head, and another mechanism prevents wobbling or misalignment of the cutting head.

It is to be appreciated that in some use cases relating to embodiments of the invention, such as tissue removal in the spine or other joint, e.g. shoulder, hip, knee, and so on, a detaching of the cutting head from the device may be a very serious matter, which may lead to the detached cutting head causing damage to the spinal cord, or to a surgeon having to perform unplanned surgery in the spine or other joint, e.g. shoulder, hip, knee, and so on, to extract the detached cutting head. A wobble or misalignment of the cutting head may also be a very serious matter, which may lead to the misaligned cutting head causing damage to nerves.

In some embodiments, even a cutting head detached from a drive shaft, or a broken drive shaft, does not allow the cutting head to extend axially more than, by way of a non-limiting example, 0.3 mm beyond its normal operation position.

In some embodiments, even a cutting head detached from a drive shaft, or a broken drive shaft, does not allow the cutting head to stray laterally more than, by way of a non-limiting example, 0.1 mm from its normal operation position.

Some drawbacks of cutting and drilling devices which include a flexible shaft include possible helixing of the flexible shaft. Helixing is a phenomenon where a central axis of the flexible shaft twists itself in a helical or corkscrew shape upon the application of torque. As the torque continues to increase, the degree of helix may become more severe. An outer casing may limit the degree of Helixing. On the other hand helixing may cause friction with the outer casing. Helixing might cause the cutting head to detach from the device; and/or cause the cutting head to wobble or mis align and cut a wrong part of a body; and/or the drive shaft to break and/or heat excessively, possibly causing thermal damage. Embodiments of the tissue removal device are frequently used at a high rotational speed, which may cause heating or early breakage. Being used inside a body, tissue parts or tissue fragments being suctioned out via the device shaft may encourage helixing.

All in all, a flexible shaft which reduces helixing can provide a potential benefit.

The present invention, in some embodiments thereof, improves on prior art designs by including a flexible shaft which minimizes helixing.

For example, cutting and drilling devices which include a drive shaft and a cutting head may suffer from possible breakage at some location along the drive shaft. Breakage at some location along the drive shaft may cause problems—it may be better to plan for breakage at a known location, such as a connection between the drive shaft and the cutting head.

The present invention, in some embodiments thereof, improves on prior art designs by including a breakable connector, such as a breakable tenon, connecting the drive shaft and the cutting head. In some embodiments, the breakable connector is designed to break at a torque less than either the cutting head or the drive shaft are designed to withstand, thus ensuring breakage by the connector. By breaking before failure of the cutting head or of the drive shaft, the breakable connector assures that the cutting head and/or drive shaft do not fail, and the cutting head does not do damage to the body. In some embodiments the breaking torque of the connector is designed to be greater than a torque specified for operating the cutting and/or drilling action.

In some embodiments the tenon is made of metal, such as stainless steel.

Some embodiments of the tissue cutting and drilling device of the present invention also incorporate one or more of the following features:
(i) an elongated shaft with a curved distal portion having a curve angle selected suitable for lumbar decompression, i.e. entering behind the vertebral lamina in the lumbar section of the spine, in a so-called posterior approach.
(ii) an elongated shaft with a curved distal portion having a curve angle selected suitable for cervical decompression, e. g. entering behind the vertebral body in the cervical section of the spine, in a so-called anterior approach.

A curved drive shaft is especially prone to heating, to early breakage. In a flexible drive shaft the curve causes a flexing back and forth of the drive shaft at a rate of the rotation, which may cause heating, and may cause breakage.

A flexible drive shaft used in context of spinal tissue removal is designed to be thin, for example in a range of 1-5 mm. Such a thin drive shaft, operating at high RPM as described elsewhere herein, and at angles of curvature as described elsewhere herein, is a thin drive shaft operating under a lot of stress, which might lead to breakage. The dimensions of the drive shaft keep the stress concentrated within a small radius. Having a safety mechanism to prevent the cutting head from flying forcefully out of the device, or even from dropping out of the device, is useful, especially taking into account the damage which may be done in the body, especially in a spine or other joint, e.g. shoulder, hip, knee, and so on.

It is noted that in case of using embodiments of the invention for treating joints other than in a spine, changes are optionally made to some features. By way of some non-limiting examples:

A length of the elongated shaft may be up to 30 cm, and may be even longer in case of hip joint treatment.

A diameter of a curve of a tip of the elongated shaft may be up to 60 mm, and may be even higher for hip treatment and for shoulder treatment.

In some embodiments, by way of a non-limiting example for joint arthroscopy procedures, the inner lumen is optionally used for suction rather than for irrigation.

In some embodiments, rotation rate of the cutting head may be lower than described elsewhere herein.

In some embodiments, a cutting head suitable for cutting softer tissue such as, by way of a non-limiting example, ligament, may be used.

According to one aspect of the present invention there is provided a device for cutting tissue from a body of a subject such as a human subject. As used herein in some embodiments, the term "cutting" refers to removing tissue based on rotation of a cutting head. Depending on the type of cutting, resulting tissue fragments may be left in the body or removed using well known approaches such as suction or mechanical collection. Removal can be effected using an embodiment of the present invention or by using dedicated tissue removal devices, such, by way of a non-limiting example, Kerrison Rongeurs, as described in www(dot)orthomedinc(dot)com/wp-content/uploads/2013/04/18-O-Spinal-Rongeurs-and-Punches(dot).pdf.

Some embodiments of the device of the present invention include an elongated device body having a curved distal portion. A portion of the elongated device body is also termed herein a shaft, or an elongated shaft, or an elongated shaft body.

As is further described herein, the elongated device body and its curved distal portion potentially enable accurate positioning of the cutting head against an internal surface of a lamina and/or a tissue impinging on a nerve fiber.

The elongated device body may be, for example, 30-250 mm in length (e.g. 104 mm) with the curved distal portion being, for example, 49-269 mm in length (e.g. either 123 mm or 116 mm depending on use) and having a radius of curvature, for example, of 4-12 mm (e.g. 9 mm). Such a radius of curvature forms an angle between the curved portion and the straight portion of elongated device body of, for example, 90-160 degrees, e.g. 105 and 135 degrees (model dependent).

The elongated device body optionally has a circular or oval cross section with an external diameter of, for example, 2-5 mm, e.g. 3.2 mm. The diameter and/or cross sectional shape of the elongated device body may be constant along its length or may vary, for example, from a larger diameter at a proximal end to a smaller diameter at a distal end or vice versa.

The elongated device body may be fabricated from any material used in surgical devices, including, for example, stainless-steel, titanium, a polymer and the like. The various device components may be fabricated using well known approaches such as casting, extrusion, machining and the like.

In some embodiments, the elongated device body includes at least one lumen which extends from a proximal end of the device body to a cutting head which may be attached to a distal end of the elongated device body. The lumen optionally follows the curvature of the elongated device body and has a diameter of, for example, 1-4 mm (e.g. 2.8 mm) which may be configured for intimately housing a drive shaft (for example, 30-100% larger than the flexible drive shaft diameter) to ensure that at least a flexible portion of the drive shaft does not kink or warp within the lumen. The lumen for containing the drive shaft is optionally centered within the elongated device body. The drive shaft extends from a motor optionally positioned within a handle optionally attached to the proximal end of the device body to the cutting head and optionally transmits rotational (optionally bidirectional) and optionally forward/backward motion to the cutting head. The drive shaft may optionally include a substantially rigid portion connected to (mechanically, via crimping, or via welding), or contiguous with a substantially flexible portion. The rigid portion optionally traverses at least some of the straight portion of the elongated device body, while the flexible portion traverses the curved portion, and optionally some of the straight portion. As is further described herein, the drive shaft may include a rigid tube crimped over an end of a flexible multi-layer cable.

The multi-layer wire cable may be configured for high torsional rigidity and low bending rigidity, potentially enabling the wire cable to rotate at high speed while bent, potentially at a small radius of curvature. The high torsional rigidity and low bending rigidity is beneficial for service in a bent form. Having a low bending rigidity potentially allows for low bending-related stress and better resistance to fatigue potentially caused by high rotation speed and/or high rotation torque. Such a wire cable may be braided, coiled or twisted from inner layers configured for maintaining high structural integrity, and optionally low torsional rigidity, and outer layers configured for maintaining high torsional rigidity. The multi-layer wire cable includes at least one inner layer, optionally more, and at least one outer layer, optionally more. In order to further enhance the ability of the cable to transmit torque to the cutting head without fraying and/or buckling and/or breaking, each of the above layers may be configured to have mechanical properties in a direction opposite to the direction of the adjacent layer. It is noted that a typical mode of failure of the multi-layer wire cable, especially when operating as part of the tissue removal device, is that the strands are eventually broken or cut. The mode of failure is typically a dynamic failure.

The wire cable core may be fabricated, for example, from seven 304V stainless-still wires (each having a diameter of, for example, 0.084 mm) twisted into a rope. Several layers of coils, e.g. 3 layers, are then wound around the rope core. Each successive coil may optionally be wound in the opposite direction of the coil which precedes it. The inner coil (closest to rope core) includes, for example, five wires (with a diameter of e.g. 0.12 mm each), the middle coil includes, for example, five wires (with a diameter of e.g. 0.14 mm each) and the outer coil includes, for example, five wires (with a diameter of e.g. 0.16 mm each).

The cable design is capable of transferring rotational and longitudinal motion, i.e. torque and rotational speed and axial force and speed, along a curved path with angles described elsewhere herein, in a manner resistant to fatigue. It is noted, however, that such paths can be fixed, as in some embodiments where the curved tip may be rigid, or variable, where the tip can accept multiple angles or curvatures before and/or during the tissue cutting, as in the prior patent application by the same inventor, PCT Published patent application WO 2012/004766.

In some embodiments the flexible drive shaft, such as, for example, the wire cable described above, has a diameter of, for example, 0.3 mm to 5 mm, e.g. 0.5 mm or 1.5 mm or 3 mm.

The elongated device body optionally includes at least one additional lumen. The additional lumen may optionally be offset from a central lumen, or may be a central lumen, and may be used for delivering and aspirating irrigation fluid, and/or for delivering medication (e.g. Steroids, Marcaine, etc.), and/or for cooling.

As is described herein, the proximal end of the elongated device body may be attached to a handle which houses a drive transmission and optionally a motor as well as electrical circuitry. The handle may be configured for allowing a user to manipulate the device and operate the motor driven cutting head. In that respect, the handle may be shaped substantially as an inverted cone with a length of, for example, 75-105 mm and a proximal diameter of, for example, 20-30 mm and a distal diameter of, for example, 5-15 mm. The handle may be fabricated as a shell composed of one or more cast, machined or injection-molded pieces. The handle may include a user interface for operating the motor, setting motor parameters (e.g. RPM and direction of rotation etc.), setting cutting time, operating and setting irrigation parameters as well as controlling adjunct devices such as a neuro-stimulation device.

Furthermore, the handle may be designed and configured such that a surgeon maintains a clear line-of-site along the device, helping the surgeon to monitor progress while cutting some tissue and avoiding tissues not targeted for cutting.

The user interface may also include a display for displaying various parameters related to the motor or to irrigation, as well as information related to the cutting head and flexible drive shaft such as temperature, mechanical integrity, cutting head position and the like, and information related to adjunct device (e.g. electrodes for neuro-monitoring) used during a procedure.

As is mentioned herein, the present device includes a cutting head having a tissue cutting portion. The tissue cutting portion may be fabricated from, for example, 17-4 pH (precipitation-hardened) stainless-steel; for example, 2.5 mm OD with, for example, 4 spiral flutes (lead angle, for example, 26 Deg, depth, for example, 0.75 mm, width, for example, 0.8 mm) each having a sharp edge forming a blade. The cutting head optionally has a shaped tip for drilling, for example, spherical, where the blades follow a dome shape to the apex of the cutting head. The cutting head optionally has a 1 mm OD, for example, shaft with a flat surface on one side, for transferring both torsional and axial integrity of the cutter connection to the flexible shaft. The outer diameter of the tissue cutting portion may be, for example, 1.5 mm-5 mm (e.g. 2.5 mm) with a spherical radius of 0.2 mm-1.25 mm, (e.g. 1.25 mm). The length of the tissue cutting portion varies depending on use from 2 mm-15 mm (e.g. 3.45-6.25 mm including sphere, 2.2-5 mm without sphere).

Due to the directional nature of cutting employed in some spinal procedures and the fact that some of the regions treated may be anatomically constrained and includes sensitive tissue (e.g. nerve fibers), some of the length of the tissue cutting portion may be covered on one or more sides by a shield fabricated from a polymer or an alloy. Such a shield can cover, for example, 90-270 degrees of the circumference of the tissue cutting portion and may be either fixed in a predetermined position (e.g. along the external curve of the curved portion) or rotatable around the cutting head.

In some embodiments, a cutting head restraining element attaches to the shield, and/or is embodied in the design of the shield.

In some embodiments, the cutting head restraining element attaches to the shaft elongated body and not to the shield.

As is mentioned herein, the present inventors have discovered that the load on the cutting head during cutting of hard tissue (bone) can lead to failure of the flexible drive shaft. When used in a potentially dangerous procedure such as laminectomy, detachment of the cutting head from the drive shaft can potentially lead to damage to surrounding nerve fibers and possible complications even if the cutting head does not actually detach from the device (e.g. the cutting head might vibrate in the housing and/or break).

The present inventors have devised a mechanism for retaining the cutting head in the device and prevent unwanted cutting head vibration and wobbling and the like if the cutting head detaches from the drive shaft.

Such a mechanism (which is described in greater detail below) potentially enables that a mechanical failure of the drive shaft, and/or breakage of the drive shaft, does not lead to detachment of the cutting head from the device or to other unexpected behaviors of the head.

In some embodiments the retaining mechanism is made mostly of stainless steel, which can be formed to the desired shape by, for example, machining, laser cutting, extrusion, photo-etching and so on.

A feature of some example embodiments of the retaining mechanism allows forward drilling by the cutting head. The cutting head of such embodiments is attached on to a drive shaft at its base, and is free at the forward cutting edge. Forward drilling is highly important in cases of a narrow anatomy, where the device cannot be introduced into a narrow gap, such as between a nerve and a bone in a spine joint, as such a gap does not exist. In such cases forward drilling potentially enables a surgeon to carve out an initial space required for introducing the tissue removal device.

The distal end of the tissue cutting portion may be smooth and/or diamond-coated to reduce impact on soft tissue such as the dural sack.

Diamond coating the tissue cutting portion enables tissue differentiation, with the tissue cutting portion cutting hard matter such as bone and not harming soft tissue.

Reference is now made to FIG. 1, which is a side cutaway view of a device 10 constructed as an example embodiment of the invention showing a handle 12, an elongated shaft body 30 and a cutting head 50.

The device 10 includes a handle 12 which houses a motor 14 which optionally includes a motor housing 16, a motor shaft 18, a bearing 20 and an optional gasket 22 for sealing the motor shaft 18. The motor 14 optionally has an easy connect/disconnect interface (motor fork) from the handle 12. The motor 14 may be a direct-drive electrical or pneumatic motor capable of rotating at, for example, 10,000 to 70,000 RPM and providing a torque of, for example, 3-10 Ncm.

The motor 14 may also includes an optional spring 24 surrounding the motor shaft 18. The spring 24 may be a part of a motor interface mechanism and optionally allows the fork to move axially until finding a proper engagement with the motor shaft 18. The handle 12 optionally also includes a port 26 for enabling access to an irrigation lumen (described herein).

An external surface of the handle 12 optionally includes a user interface for controlling the motor 14 and optionally for controlling flow through the port 26.

The handle 12 may be connected to elongated shaft body 30 which includes a substantially linear portion (A) contiguous with or connected to a curved portion (B). The angle between the linear portion A and the curved portion B of the elongated shaft body 30 may be for example, 105 degrees (indicated in FIG. 1 by a).

The elongated shaft body 30 optionally also includes a central lumen 32 traversing the length thereof. The lumen 32 may be configured for housing a drive shaft 34 and may be, for example, 30-100% larger in diameter than the diameter of drive shaft 34.

The drive shaft 34 may be connected at a proximal end thereof to the motor shaft 18 via a mechanical joint capable of allowing easy attachment/detachment of the handle to the motor as well as torque transfer from the motor to the drive shaft 34, and a distal end thereof to the cutting head 50 (further described below).

The drive shaft 34 may be fabricated as a single contiguous cable having a rigid portion and a flexible portion (e.g. a single contiguous cable with a rigid portion and a flexible portion corresponding to the linear A and curved B portions of elongated shaft body 30. Alternatively the drive shaft 34 may be fabricated by attaching a rigid tubular portion to an end of a flexible portion (such as a multi-layer cable) by, for example, crimping the rigid tubular portion over the flexible cable. The latter configuration is presently considered advantageous as far as costs and sealing considerations are concerned—a rigid tube may be easier to seal.

In some embodiments, the flexible portion is optionally fabricated from a cable with 4-5 layers as described above.

The elongated shaft body 30 may optionally also include at least one fluid lumen 36 running between the elongated shaft body 30 and the motor shaft 18 (for example, co-axial with central lumen 32); the fluid lumen 36 may be in fluid communication with the port 26 and optionally includes an opening 38 (a cavity below distal bearing 20 where fluid can come out of the lumen in the handle and flow in the elongated shaft body 30) at a distal end of elongated device body 30. The fluid lumen 36 can be used for delivering a fluid to the site of tissue cutting, for irrigating the tissue and/or removing debris, and/or cooling the cutting head 50, and/or for delivering a medication to the tissue (e.g. anti-inflammatories, anesthetics, etc.) and/or for applying suction thereto.

In some embodiments the drive shaft optionally includes grooves and/or fins which propel fluid to or evacuate fluid from the distal end of the drive shaft, which is a vicinity of the cutting head.

Figure 2:
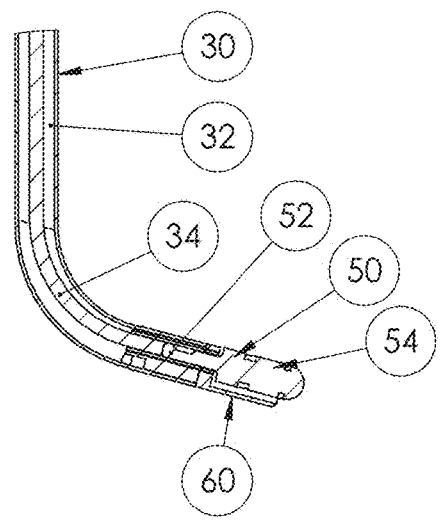
FIG. 2 is a magnified view of a circled distal portion of the device of FIG. 1.

Reference is now made to FIG. 2, which is a magnified view of a circled distal portion of the device 10 of FIG. 1.

As is more clearly shown in FIG. 2, the device 10 further includes a cutting head 50, a first portion 52 of which extends into the lumen 32, and is connected to the drive shaft 34. A tissue cutting portion 54 of the cutting head 50 may be configured for cutting and/or drilling tissue and as such may include cutting blades and/or cutting grooves to assist in removal of debris and may be shaped as described below.

A shield 60 may be optionally attached to a distal end of the elongated device body 30 and may be configured so as to cover one or more sides of the tissue cutting portion 54 in order to provide a barrier between cutting blades 36 and non-treated tissues.

The shield 60 may be fixed in position to cover, for example, 45-270 degrees of the tissue cutting portion 54, e.g. 172 degrees of the tissue cutting portion 54. The shield may cover a length of, for example 1-13.75 mm (e.g. 5 mm for a long version and 2.65 mm for short version) of the external cutting surface of the tissue cutting portion 54, i.e. the surface which corresponds to the outer curvature of the curved portion B. This potentially enables positioning of tissue cutting portion 54 against a target tissue (e.g. lamina) and pulling of device 10 towards a user to effect cutting while ensuring that the outer side of the tissue cutting portion 54 (which may be covered by the shield 60) does not accidentally contact tissue.

In some embodiments, the shield 60 can be manually rotated around the tissue cutting portion 54 of the cutting head (prior to, or during use of the device 10) to select the shielded sector of the tissue cutting portion 54.

As is further described herein, a potential problem for tissue cutting devices which employ flexible drive shafts is breakage of the drive shaft. Since the cutting head of such devices may be connected to the drive shaft, such breakage can lead to a change in cutting head rotation which can lead to vibration and wobbling of the cutting head (which can lead to loss of control, cutting head breakage, loss of cutting head etc.).

Figure 3:
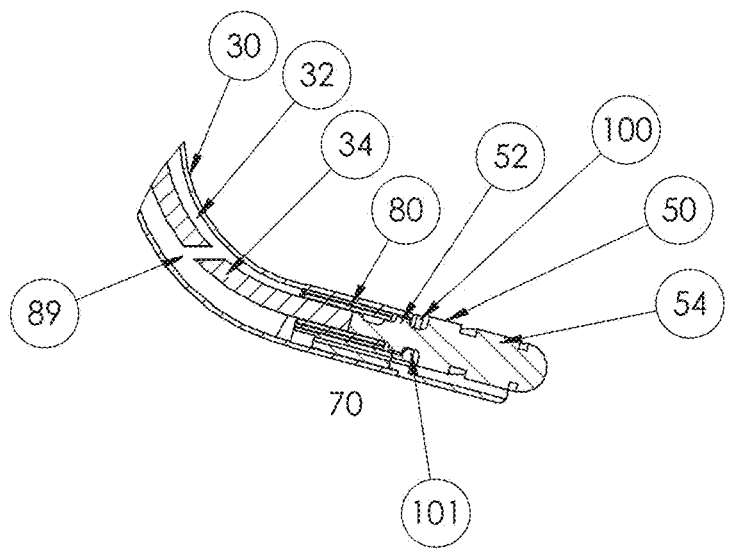
FIG. 3 is a magnified view of a distal portion of a device constructed as an example embodiment of the invention showing a cutting head and a broken drive shaft.

Reference is now additionally made to FIG. 3, which is a magnified view of a distal portion of a device constructed as an example embodiment of the invention showing a cutting head 50 and a drive shaft 34 broken at some location 89.

FIG. 3 depicts some of the components depicted in earlier FIGS. 1 and 2, referenced with the same reference numbers.

In order to traverse these limitations of prior art devices, the device 10 of some example embodiment of the present invention optionally includes a safety mechanism, a retainer 70 for retaining the cutting head 54 when detached from drive shaft 34.

As used herein, the term "retaining" refers to maintaining the cutting head 50 in physical association with a housing 80, and in some embodiments also ensuring that cutting head 50 does not lose its functional direction (e.g. does not wobble, vibrate).

In some embodiments the retaining includes limiting movement of the cutting head 50 axially along the direction of the elongated shaft body.

In some embodiments the retaining includes limiting movement of the cutting head 50 laterally across the direction of the elongated shaft body.

Experiments conducted by the present inventor showed that although a flexible drive shaft 34 provides excellent cost-performance, the flexible drive shaft 34 may be prone to degrade as a result of repeated stress.

In some embodiments a flexible shaft is chosen together with a use of a retainer 70 implemented as a safety mechanism.

In some embodiments, the safety mechanism is based on having a portion of the cutting head 50 be narrower, and a portion of the cutting head 50 be wider and having a safety component which interferes with motion of the cutting head by not allowing the wide portion to pass beyond the safety component.

In some embodiments, the wider portion is approximately 0.1-0.2 mm larger in diameter than the safety component; enough to avoid passing the safety mechanism, yet potentially not enlarging the tip of the device, which needs to be low-profile.

Figure 4:
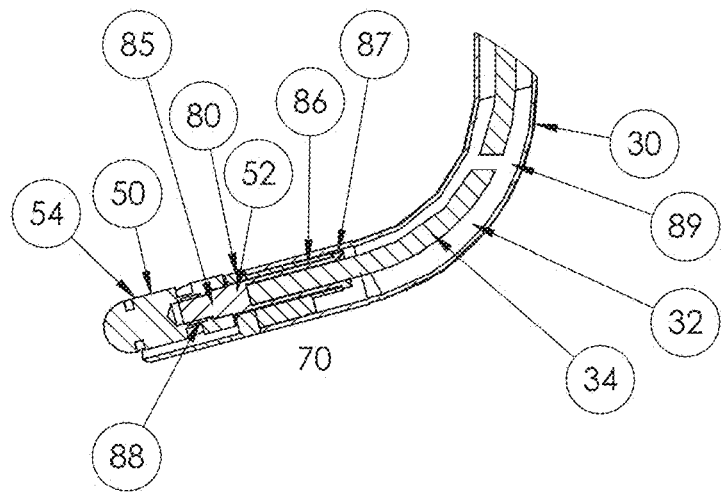
FIGS. 4, 5 and 6A are magnified views of a distal portion of an example device constructed as an example embodiment of the invention, showing several embodiments of mechanisms for securing a cutting head to a device body.
Figure 5:
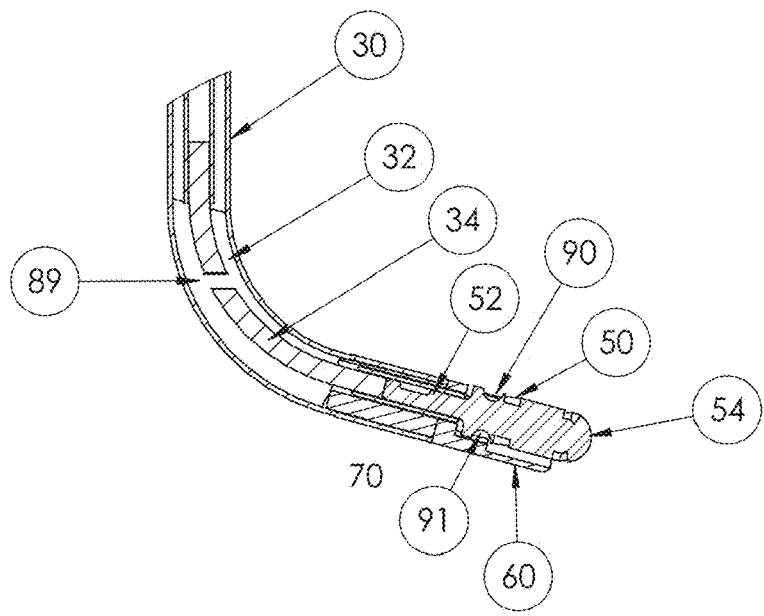
Figure 6A:
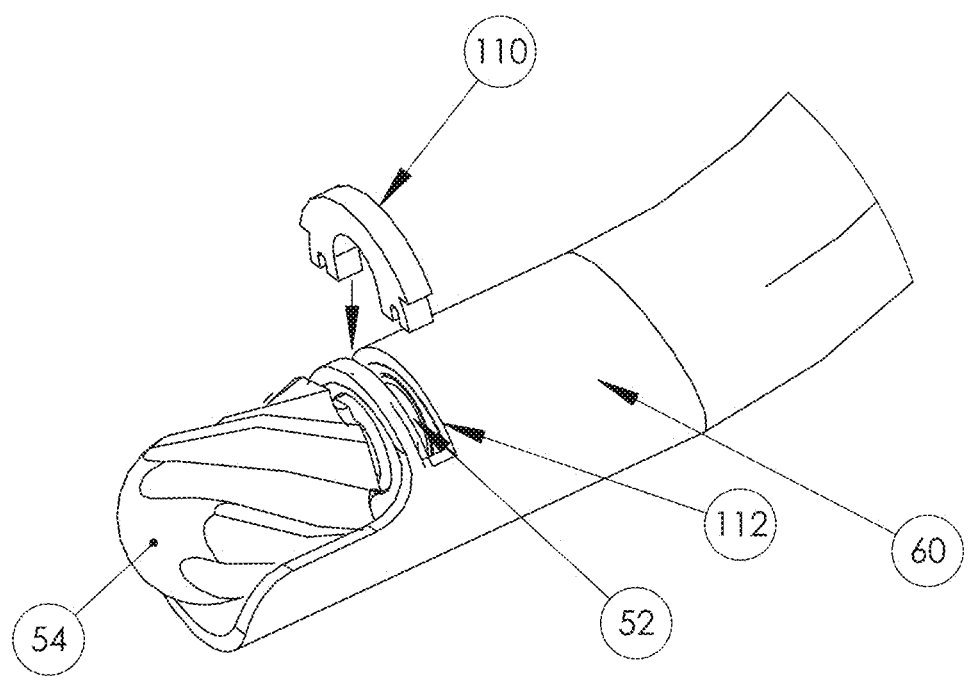

Reference is now additionally made to FIGS. 4, 5 and 6A, which are magnified views of a distal portion of an example device constructed as an example embodiment of the invention, showing several embodiments of mechanisms 70 for securing a cutting head to a device body.

FIGS. 4-6A-N depict some of the components depicted in earlier FIGS. 1-3, referenced with the same reference numbers.

FIGS. 3-6A-N illustrate several configurations of the mechanism 70. In the configuration depicted in FIGS. 3-6A-N, the cutting head 50 is held axially in place rather than held in the device 10 by a single component such as the drive shaft 34 cable (which may lead to detaching following cable failure or drive shaft-to-cutting head connection failure).

In an embodiment shown in FIG. 3, the first portion 52 of the cutting head 50 includes a circumferential groove 101; a narrowing 100 in housing 80 which may be inserted into the groove 101 without a distal end of the housing 80 contacting the cutting head 50. When a failure of the drive shaft 34 occurs (indicated at location 89 in FIG. 3) the narrowing 100 prevents the cutting head 50 from being detached from the device 10. When a failure of the drive shaft 34 to the cutting head 50 connection occurs, the narrowing 100 prevents the cutting head 50 from being detached from the device 10.

In an embodiment shown in FIG. 4, the cutting head 50 may be connected via the first portion 52 of the cutting head 50 to the drive shaft 34 using a connector 85. The connector 85 optionally includes a distal end 88 which may be threaded to the cutting head 50 and a proximal end 86 which may be crimped around the drive shaft 34. The connector 85 optionally includes an enlarged diameter member 87 such that when the drive shaft 34 fails (such as at location 89), the housing 80 prevents the cutting head 50 from being detached from the device 10.

In an embodiment shown in FIG. 5, the cutting head 50 includes a circumferential groove 91; a cut in the shield 60 forms a flap 90 (optionally a flap of metal) which may be bent and inserted into the circumferential groove 91 without impeding movement of the cutting head 50. When a drive shaft 34 fails (such as at location 89), the flap 90 prevents the cutting head 50 from being detached from the device 10.

Figure 6D:
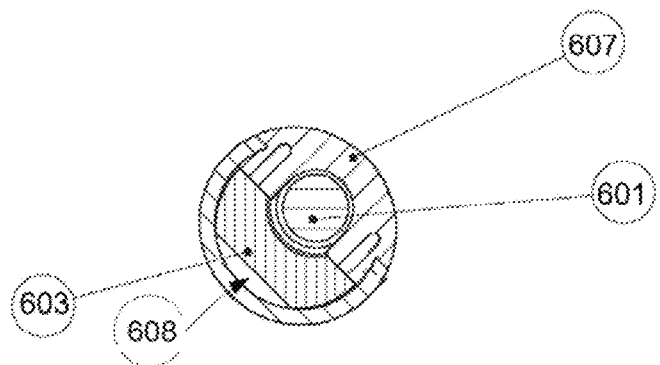
FIGS. 6B, 6C and 6D are magnified views of a distal portion of the example device of FIG. 6A.
Figure 6C:
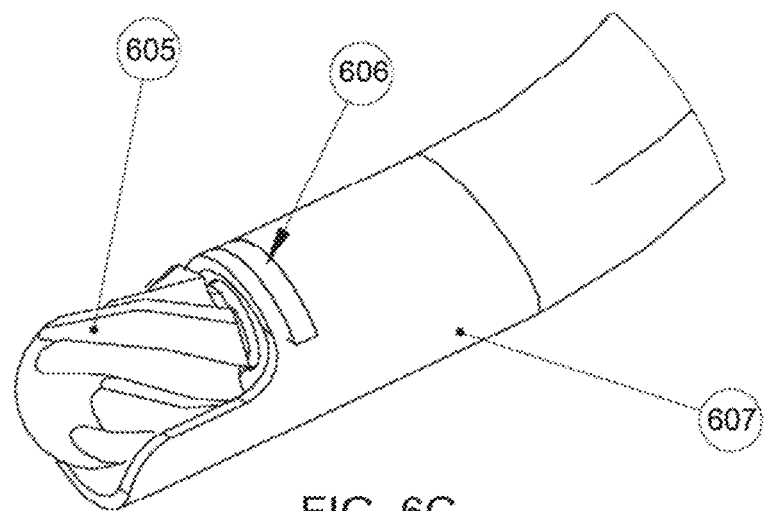
Figure 6B:
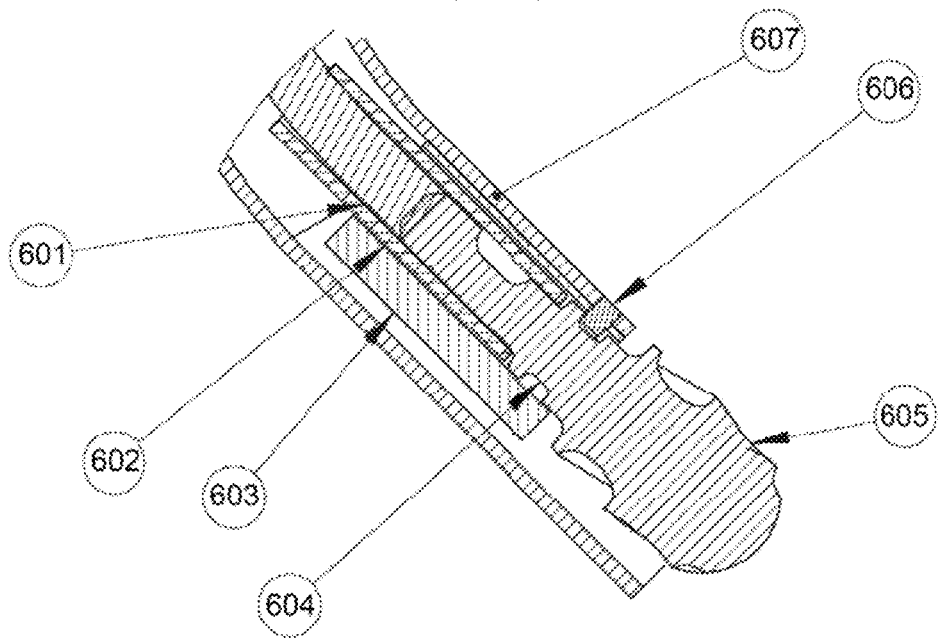
Figure 6F:
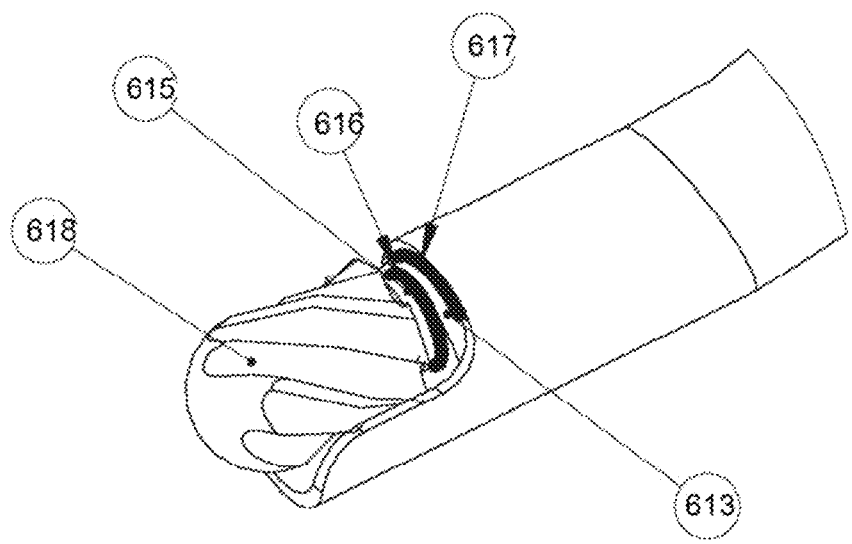
FIGS. 6E and 6F are magnified views of a distal portion of yet another example device constructed as an example embodiment of the invention.
Figure 6E:
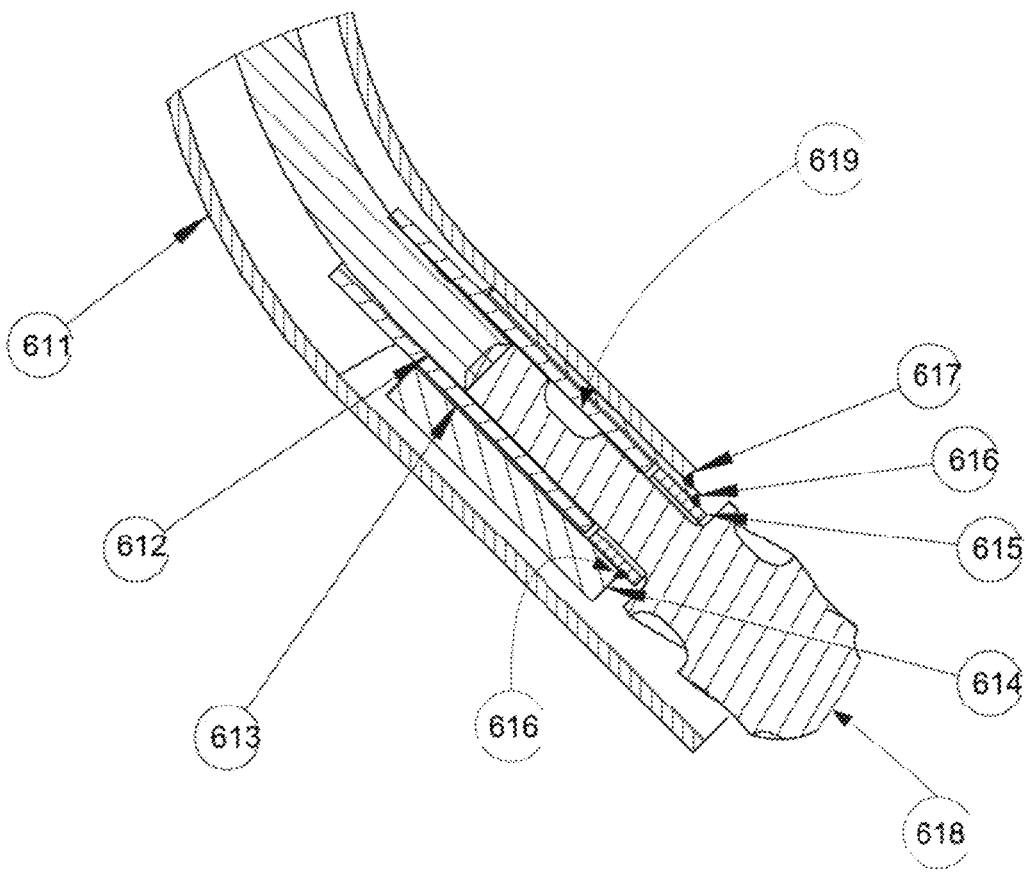
Figure 6H:
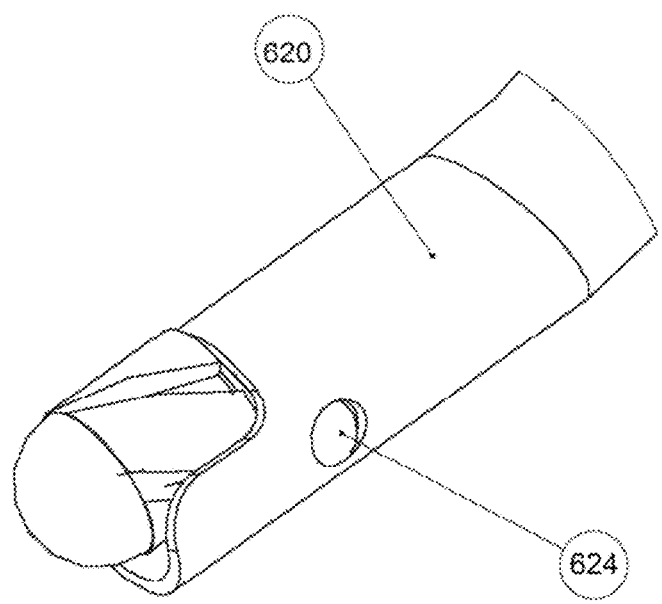
FIGS. 6G and 6H are magnified views of a distal portion of still another example device constructed as an example embodiment of the invention.
Figure 6G:
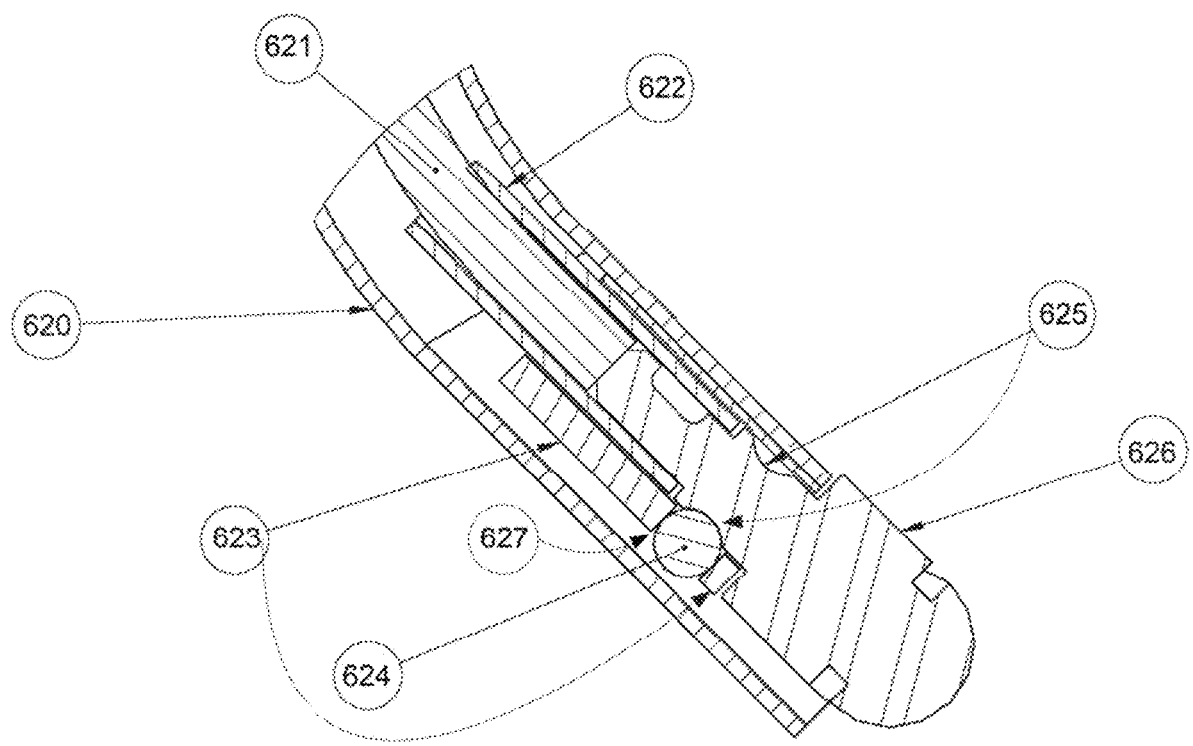
Figure 6I:
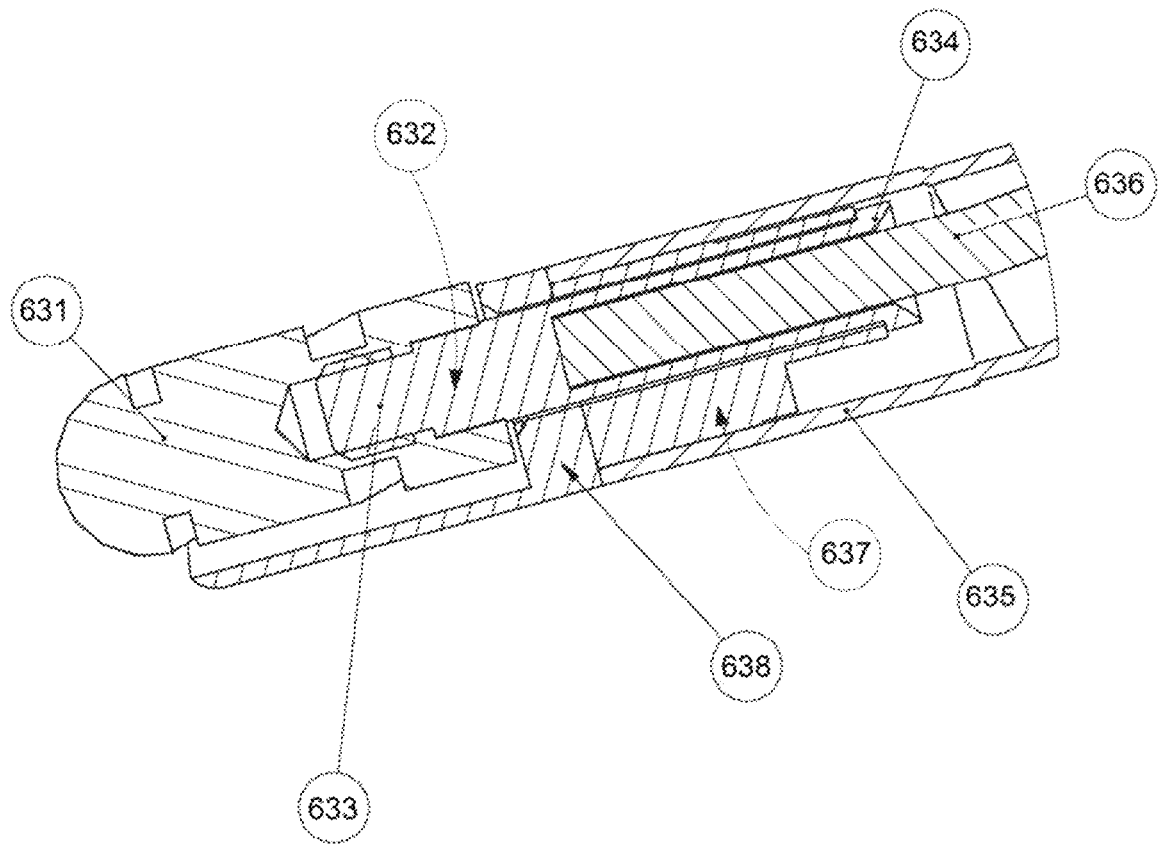
FIG. 6I is a magnified view of a distal portion of the example device of FIG. 4.
Figure 6K:
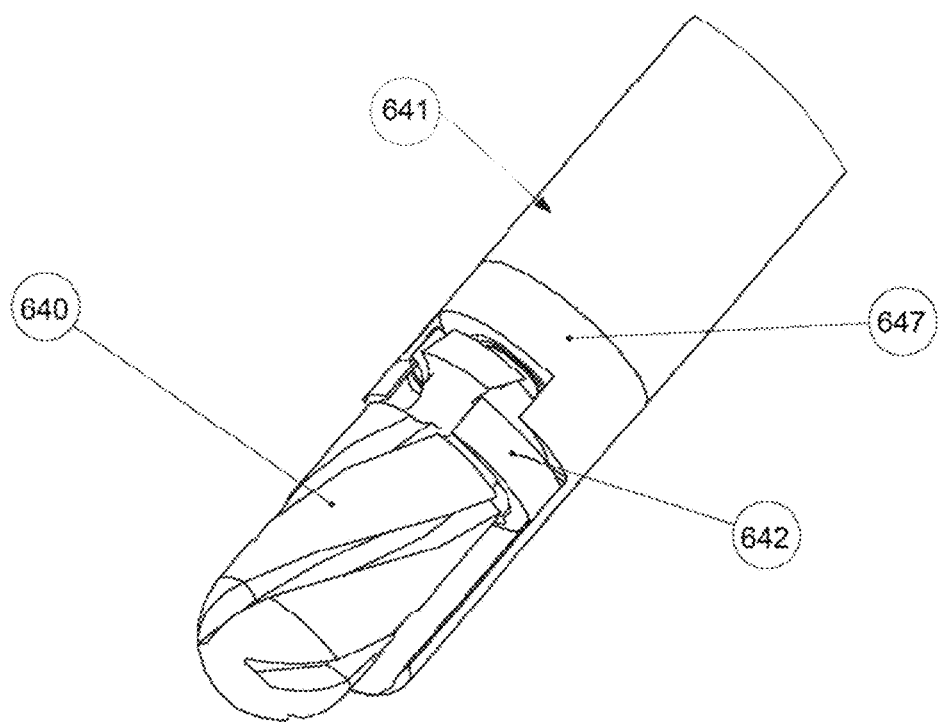
FIGS. 6J and 6K are magnified views of a distal portion of the example device of FIG. 5.
Figure 6J:
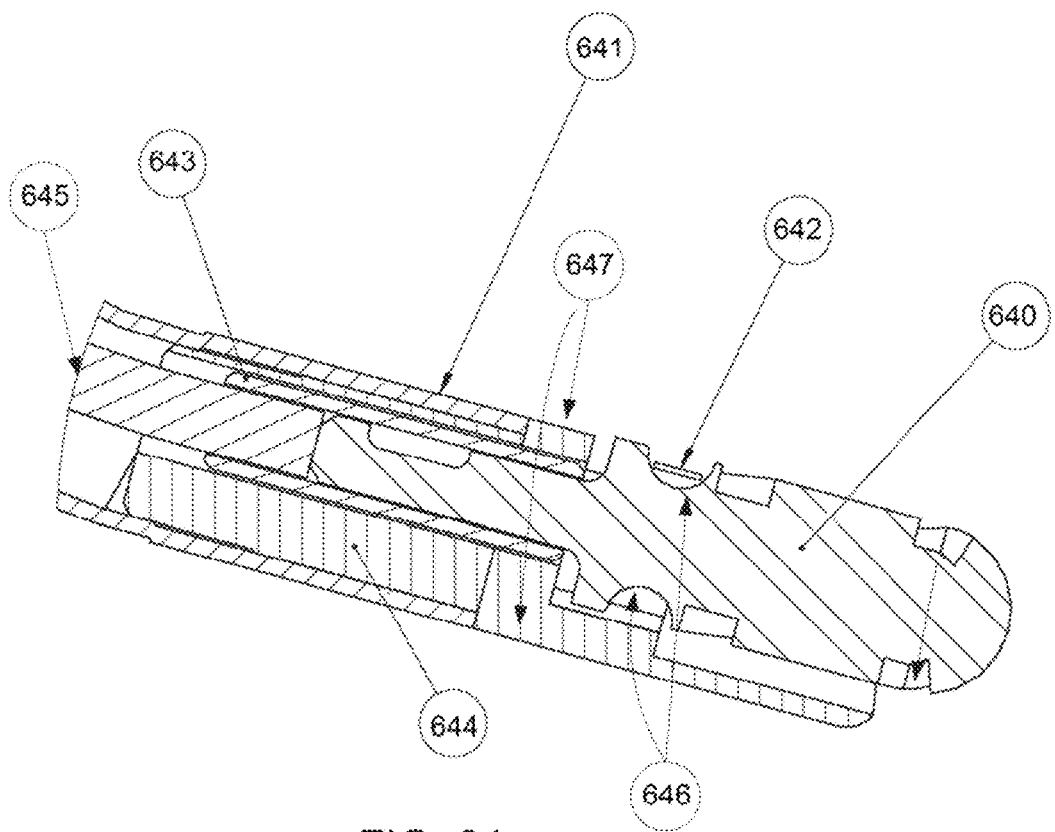
Figure 6M:
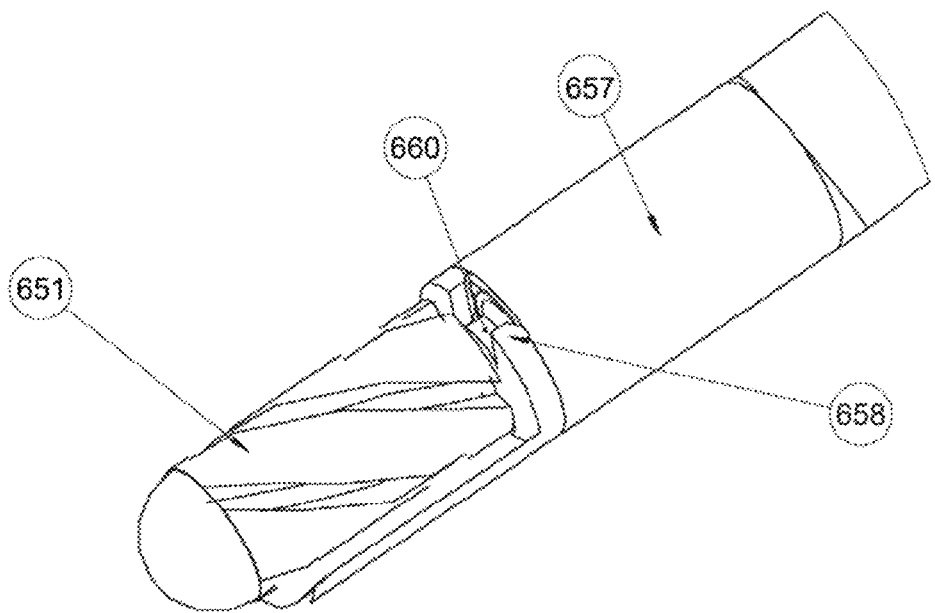
FIGS. 6L and 6M are magnified views of a distal portion of the example device of FIG. 3.
Figure 6L:
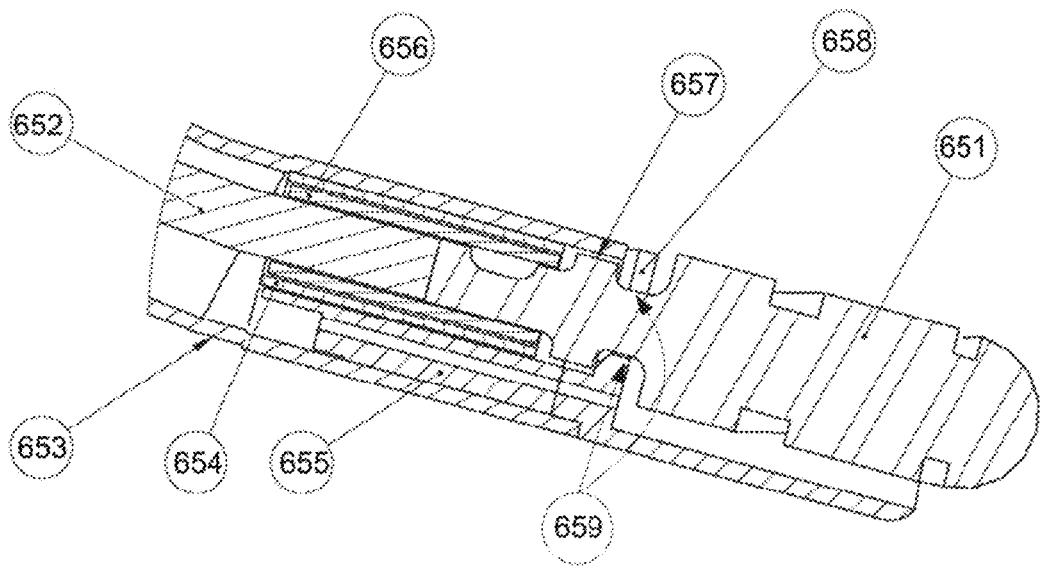
Figure 6N:
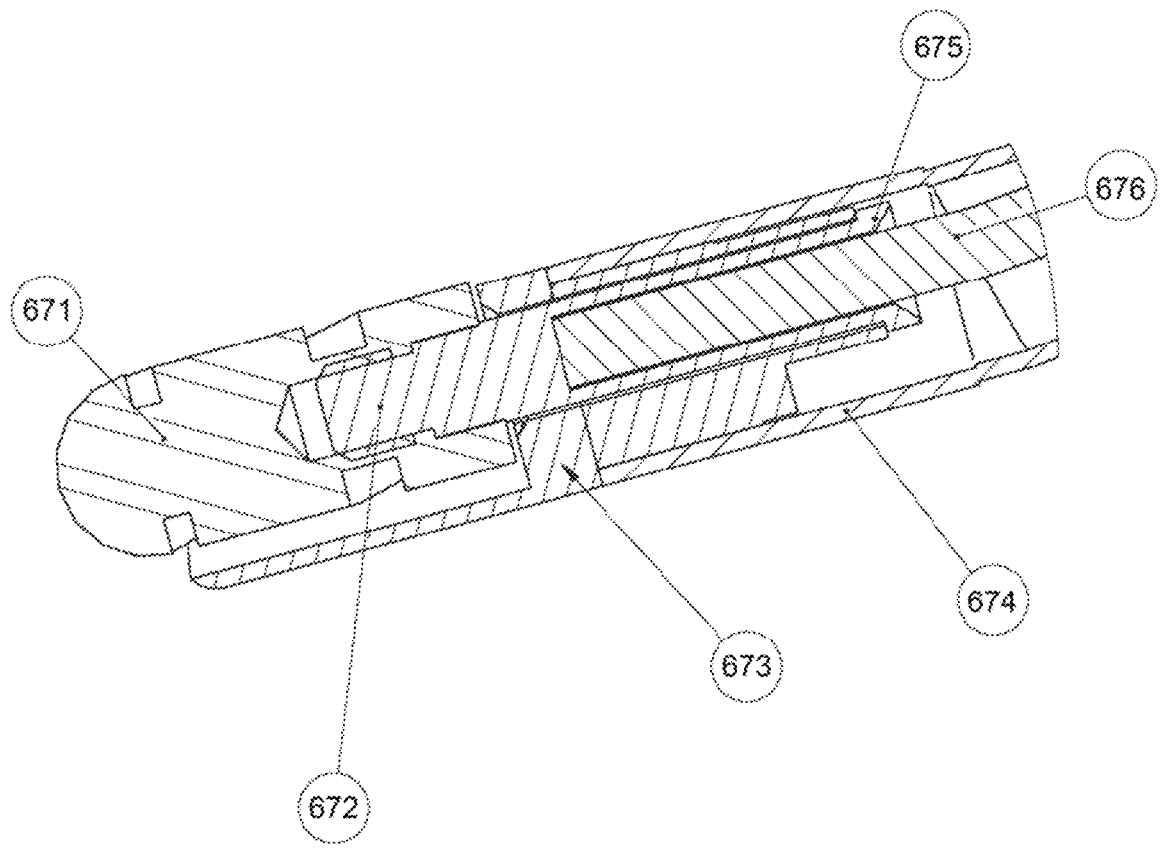
FIG. 6N is a magnified view of a distal portion of still another example device constructed as an example embodiment of the invention.

In an embodiment shown in FIG. 6A, a safety tenon 110 may be inserted through groove 112 in the shield 60, and positioned at a gap between the first portion 52 of the cutting head 50 and connector 85 (not shown in FIGS. 6A-N). If the drive shaft 34 fails (such as at location 89), the safety tenon 110 prevents the cutting head 50 from being detached from the device 10.

In some embodiments, a component which retains the cutting head, such as, for example, the flap 90 or the safety tenon 110, is designed to have low friction with the cutting head.

In some embodiments the low friction is achieved by reducing or eliminating contact between the rotating cutting head and the component which retains the cutting head.

In some embodiments the low friction is achieved by using a low friction, preferably bio-compatible material at points of contact between the rotating cutting head and the component which retains the cutting head.

In some embodiments, the component which retains the cutting head, such as, for example, the flap 90 or the safety tenon 110, is designed to limit time of use of the device, by wearing out and interfering with rotation of the cutting head.

In some embodiments, the Mean Time Between Failure (MTBF) of the retaining mechanism is at least two times the MTBF of the drive shaft under operating conditions such as listed herein for rotational rate and/or torque and/or angle of curvature of the drive shaft.

In some embodiments, the retaining mechanism is designed such that the probability of breakage of the retaining mechanism under operating conditions such as listed herein is greater than that of the drive shaft and/or the drive shaft-to-cutting head connection. For example, the probability of breakage of the retaining mechanism may be two times or ten time or 50 times as great as the probability of breakage of the drive shaft and/or the drive shaft-to-cutting head connection.

Embodiments of the device 10 may be used in a variety of spine procedures including but not limited to Laminotomy, foraminotomy, facetectomy, discectomy and the like.

Additional Example Embodiments

Reference is now made to FIGS. 6B, 6C and 6D, which are magnified views of a distal portion of the example device of FIG. 6A.

FIG. 6B is a cross sectional view of the distal portion of the example device, the cross section being along a length of the distal section of the device.

FIG. 6C is an isometric view of the distal portion of the example device.

FIG. 6D is a cross sectional view of the distal portion of the example device, the cross section being perpendicular to the axis of the distal section of the device.

FIGS. 6B, 6C and 6D depict a distal section of the device including a cutting head 605, an elongated shaft body 607, a drive shaft 601, and a cutter housing 603.

The cutter housing 603 serves as a bearing surface for the cutting head 605.

The cutting head 605 has a groove 604, into which a retaining tenon 606 intrudes, so that if the cutting head 605 should be detached from the drive shaft 601, the cutting head 605 will not detach from the device, by virtue of being retained by the tenon 606 to the elongated shaft body 607.

In some embodiments, as depicted in FIGS. 6B and 6C the elongated shaft body 607 may be integrated with a shield on a side of the cutting head 605.

In some embodiments, as depicted in FIG. 6B the drive shaft 601 and the cutting head 605 are attached to each other by crimping a sleeve 602 over the ends of the drive shaft 601 and the cutting head 605.

In some embodiments, as depicted in FIG. 6D, the cutter housing 603 is shaped so as to leave a space 608 between the cutter housing 603 and the elongated shaft body 607.

Reference is now made to FIGS. 6E and 6F, which are magnified views of a distal portion of yet another example device constructed as an example embodiment of the invention.

FIG. 6E is a cross sectional view of the distal portion of the example device, the cross section being along a length of the distal section of the device.

FIG. 6F is an isometric view of the distal portion of the example device.

FIGS. 6E and 6F depict a distal section of the device including a cutting head 618, an elongated shaft body 611, a drive shaft 612, a drive shaft sleeve 613, and a cutter housing 614.

The cutter housing 614 serves as a bearing surface for the cutting head 618, and in the embodiment of FIGS. 6E and 6F the cutter housing 614 is also attached, by way of a non-limiting example welded 616, to a short sleeve 615. The short sleeve 615 also serves as a bearing surface for the cutting head 618. The short sleeve 615 is also attached, by way of a non-limiting example welded 617, to the elongated shaft body 611.

In some embodiments, the cutting head 618 has a groove 619, into which the drive shaft sleeve 613 is optionally intruding, by way of a non-limiting example by being crimped into the groove 619, so that if the cutting head 618 should be detached from the drive shaft 612, the cutting head 618 will not detach from the device, by virtue of being retained by the drive shaft sleeve 613.

In some embodiments, as depicted in FIGS. 6B and 6C the elongated shaft body 611 may be integrated with a shield on a side of the cutting head 618.

In some embodiments, welding attachments are optionally formed by micro-laser welding, which common in the medical device industry produces clean, biocompatible welds, and is an accurate process.

Reference is now made to FIGS. 6G and 6H, which are magnified views of a distal portion of still another example device constructed as an example embodiment of the invention.

FIG. 6G is a cross sectional view of the distal portion of the example device, the cross section being along a length of the distal section of the device.

FIG. 6H is an isometric view of the distal portion of the example device.

FIGS. 6G and 6H depict a distal section of the device including a cutting head 626, an elongated shaft body 620, a drive shaft 621, a drive shaft sleeve 622, and a cutter housing 623.

The cutter housing 623 includes a hole 627, into which a pin 624 is inserted, the pin also protruding into a groove 625 in the cutting head 626. The pin 624 retains the cutting head 626 attached to the cutter housing 623 and optionally also to the elongated shaft body 620, if the cutting head 626 should happen to becomes detached from the drive shaft 621.

Reference is now made to FIG. 6I, which is a magnified view of a distal portion of the device of FIG. 4.

FIG. 6I is a cross sectional view of the distal portion of the example device, the cross section being along a length of the distal section of the device.

FIG. 6I depicts a distal section of the device including a cutting head which includes two parts—a first part 631 which includes cutting edges and/or surfaces, and a second part 632 which attaches to a drive shaft 636. FIG. 6I also depicts an elongated shaft body 635, and a cutter housing 637.

The first part 631 of the cutting head is optionally threaded 633 onto the second part 632 of the cutting head.

In some embodiments the thread connecting the first part and the second part is designed according to an intended direction of rotation of the cutting head, so as not to loosen under rotation.

In some embodiments the second part 632 of the cutting head is wider 634 at the drive shaft 636 end.

In some embodiments the second part 632 of the cutting head is attached to the drive shaft 636 by additional threading. In some embodiments the second part 632 of the cutting head is attached to the drive shaft 636 by crimping the second part 632 of the cutting head onto the drive shaft 636.

Reference is now made to FIGS. 6J and 6K, which are magnified views of a distal portion of the device of FIG. 5;

FIG. 6J is a cross sectional view of the distal portion of the example device, the cross section being along a length of the distal section of the device.

FIG. 6K is an isometric view of the distal portion of the example device.

FIGS. 6J and 6K depict a distal section of the device including a cutting head 640, an elongated shaft body 641, a drive shaft 645, a drive shaft sleeve 643, and a cutter housing 644.

The cutting head 640 includes a groove 646, onto which a snap 642 is bent. The snap 642 retains the cutting head 640 attached to the elongated shaft body 641 if the cutting head 640 happens to detach from the drive shaft 645.

In some embodiments the snap 642 is part of the elongated shaft body 641.

In the embodiment depicted in FIGS. 6J and 6K, a shield 647 is attached to a distal end of the elongated shaft body 641, and the snap 642 is part of the shield 647 or attached to the shield 647.

In some embodiments the snap 642 is made of a springy metal.

In some embodiments the snap 642 is made of a plastic.

Reference is now made to FIGS. 6L and 6M, which are magnified views of a distal portion of the device of FIG. 3;

FIG. 6L is a cross sectional view of the distal portion of the example device, the cross section being along a length of the distal section of the device.

FIG. 6M is an isometric view of the distal portion of the example device.

FIGS. 6L and 6M depict a distal section of the device including a cutting head 651, an elongated shaft body 653, a drive shaft 652, a crimping tube 656 which connects the drive shaft 652 to the cutting head 651, a drive shaft sleeve 654, and a cutter housing 655.

FIGS. 6L and 6M also depict a shield 655.

The cutting head 651 of FIGS. 6L and 6M has a groove 659 and a shoulder 657, and the distal end of the elongated shaft body 653 is attached to a slotted shape 658, such that the groove 659 of the cutting head 651 enters a slot in the slotted shape 658, and the shoulder 657 of the cutting head 651 is wider than the slot. If the cutting head 651 happens to detach from the drive shaft 652, the cutting head 651 is prevented from sliding out the distal end of the device by the shoulder 657 of the cutting head 651 being wider than the slot of the slotted shape 658.

An Example Embodiment of a Device with a Replaceable Cutting Head

Reference is now made to FIG. 6N, which is a magnified view of a distal portion of still another example device constructed as an example embodiment of the invention.

FIG. 6N is a cross sectional view of the distal portion of the example device, the cross section being along a length of the distal section of the device.

FIG. 6N depicts a distal section of the device including a cutting head 671, an elongated shaft body 674, a drive shaft 676, and a cutter housing 673.

The cutting head 651 of FIG. 6N is a cutting head designed to be optionally replaceable. The cutting head 651 is removably attached to a cutting head connector 672, and the cutting head connector 672 is attached to the drive shaft 676.

The cutting head connector 672 is optionally wider at its base than a drive shaft sleeve or a cutter housing, as described above with reference to FIG. 6I.

In some embodiments the cutting head connector 672 is attached to the cutting head 631 by threading.

In some embodiments the cutting head connector 672 is attached to the cutting head 631 by a pin (not shown) or by a tenon (not shown).

The option of replacing cutting heads provides for optionally replacing cutting head shapes and sizes so as to optimally fit a specific task, as well as for optionally replacing worn out cutting heads.

In some embodiments replacing cutting heads is designed to be performed using hand tools.

Some Example Embodiments in Example Uses

Figure 7A:
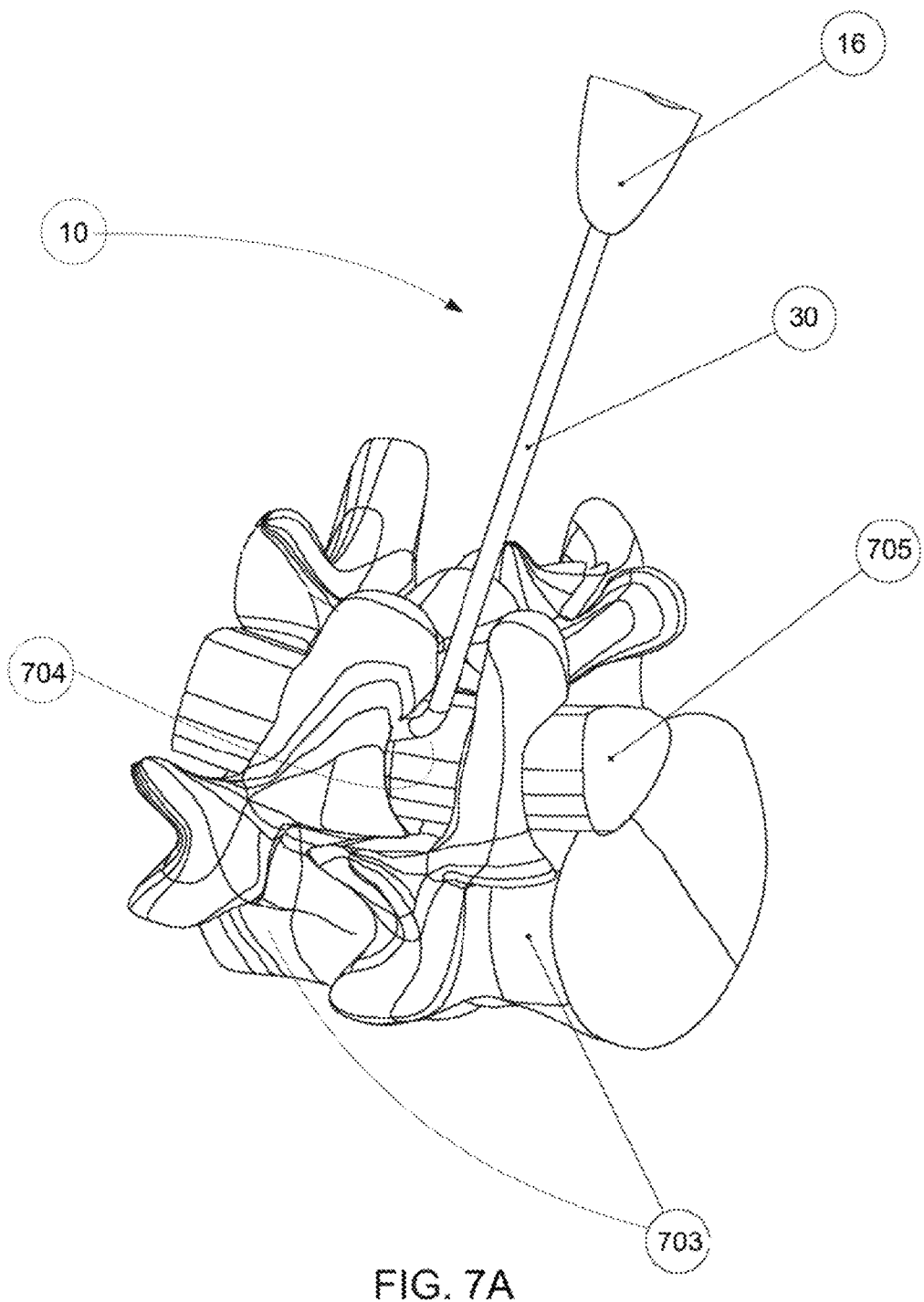
FIG. 7A is a simplified illustration of a device constructed according to an example embodiment of the invention in use in a laminectomy procedure.

Reference is now additionally made to FIG. 7A, which is a simplified illustration of a device 10 constructed according to an example embodiment of the invention in use in a laminectomy procedure.

FIG. 7A depicts some of the components depicted in earlier FIGS. 1-6A, referenced with the same reference numbers.

FIG. 7A depicts the device 10 with the cutting head (not shown), at the distal end of the elongated shaft body 30, inserted between bone of vertebra 703 and a dura mater membrane 704 surrounding a spinal cord 705.

Figure 7C:
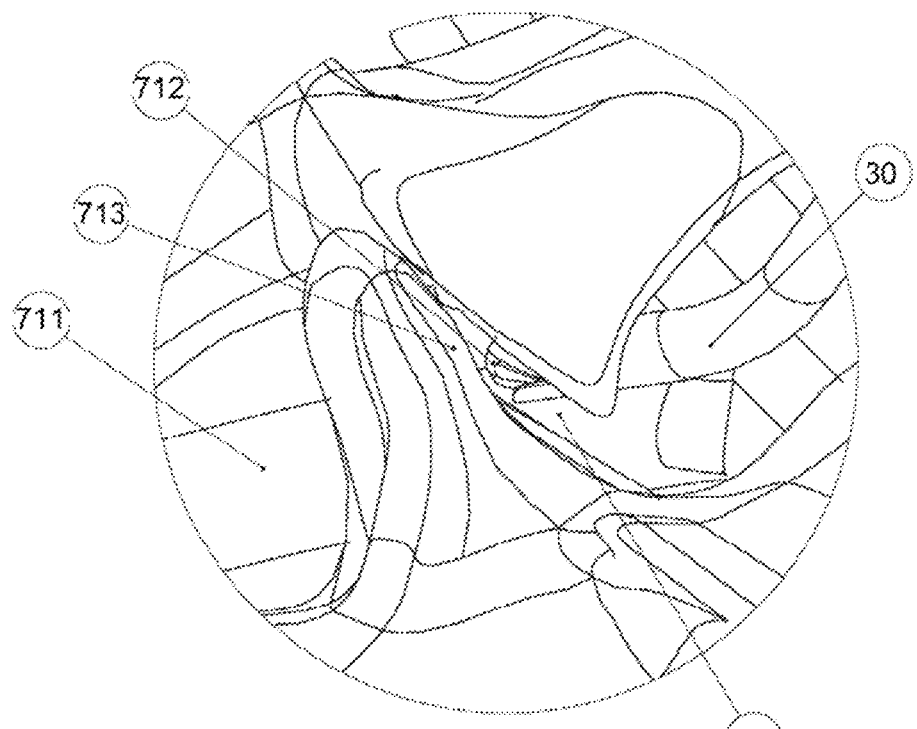
FIGS. 7B and 7C are simplified illustrations of a device constructed according to an example embodiment of the invention in use in a foraminotomy procedure.
Figure 7B:
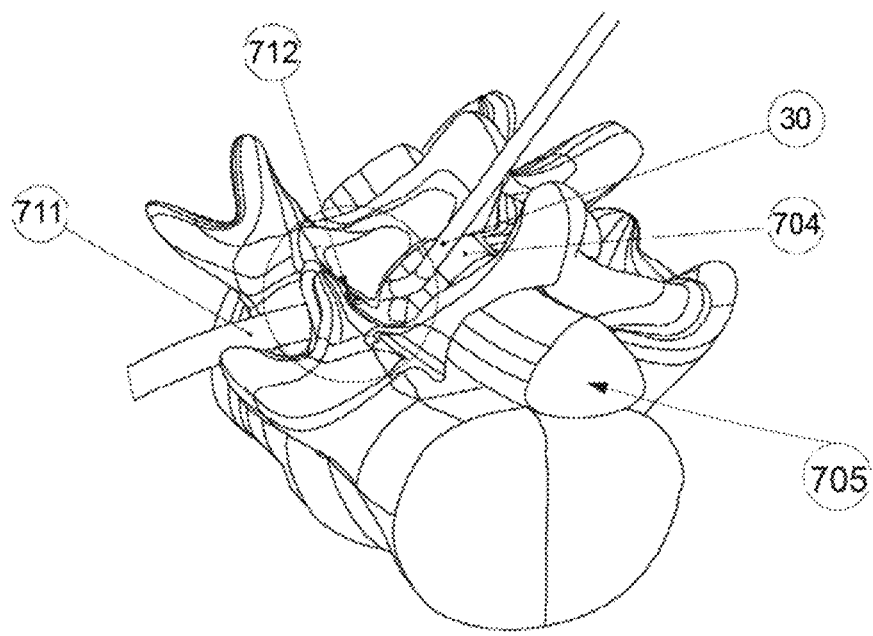

Reference is now made to FIGS. 7B and 7C, which are simplified illustrations of a device constructed according to an example embodiment of the invention in use in a foraminotomy procedure.

FIG. 7C is a larger view of the circled area within FIG. 7B.

FIGS. 7B and 7C depict the elongated shaft body 30 with a cutting head 712 at a distal end of the elongated shaft body 30, inserted between bone of vertebra 703 and a dura mater membrane 704 surrounding a spinal cord 705. FIGS. 7B and 7C also depict a nerve root 711.

The cutting head 712 of FIGS. 7B and 7C is optionally a cutting head configured for forward drilling FIG. 7C also depicts a facet joint 713.

Figure 7E:
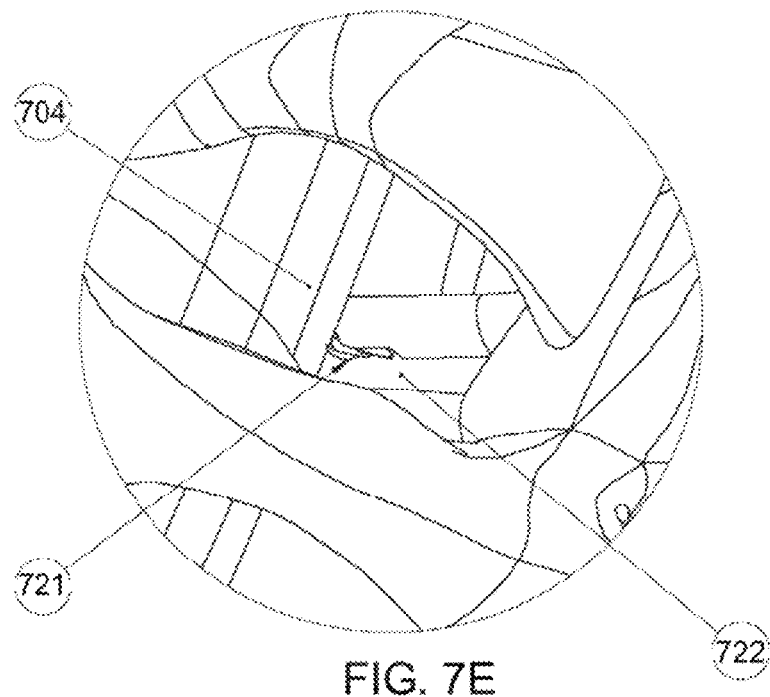
FIGS. 7D and 7E are simplified illustrations of a device constructed according to an example embodiment of the invention in use in a discectomy procedure.
Figure 7D:
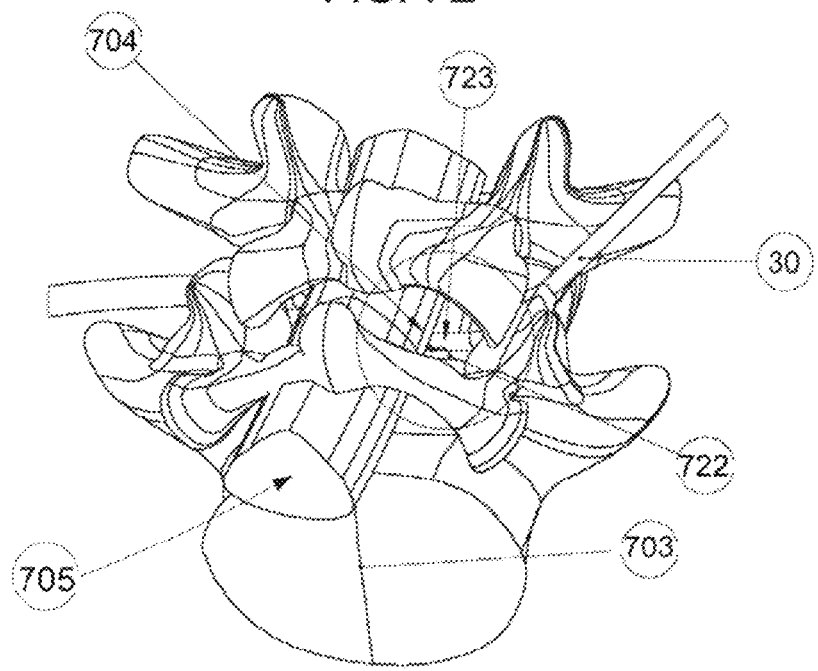

Reference is now made to FIGS. 7D and 7E, which are simplified illustrations of a device constructed according to an example embodiment of the invention in use in a discectomy procedure.

FIG. 7E is a larger view of the circled area within FIG. 7D.

FIGS. 7D and 7E depict the elongated shaft body 30 with a cutting head 721 at a distal end of the elongated shaft body 30, inserted between bone of vertebra 703 and a dura mater membrane 704 surrounding a spinal cord 705. FIGS. 7D and 7E also depict a disc protrusion 722.

Embodiments of the device 10 may be particularly useful in procedures where decompression of an impinged nerve is required with preservation of enough healthy tissue to maintain the structural strength and stability of the spinal column. In such cases, an "inside-out" approach for removing boney tissue in contact with a nerve and preserving surrounding bone (laminotomy) is advantageous.

A typical lumbar laminotomy may be initiated by making an incision through the skin, fat and fascia in an appropriate position and optionally verifying access, optionally by fluoroscopy. The spinous-process may be exposed and the par-vertebral muscles optionally spread to allow access to the ligamentum flavum. A small opening may be made in the ligamentum flavum using a scalpel (and additional surgical tools e.g. bone RONGEUR), through which the elongated shaft body 30 carrying the cutting head 50 may be advanced towards the central foramen, just behind the lamina and pushed against the dural sack (as depicted in FIG. 7A).

The cutting head 54 may be then rotated at a speed of, for example, 15,000 rpm, and bone tissue may be cut according to a magnitude and direction of a force applied by a surgeon on the handle 12. Bone debris particles are optionally washed away from the tissue cutting portion 54 of the cutting head 50 by a fluid which may be forced out of the lumen 32.

Following bone cutting (for example, 2-3 minutes later), the surgeon may evaluate the size of a decompressed location by pulling out the elongated shaft body 30 and inserting a sizing tool (e.g. spud) (not shown) into the newly created gap between the lamina and the dural sack.

An Example Embodiment of Flexible Drive Shaft Design

Figure 8C:
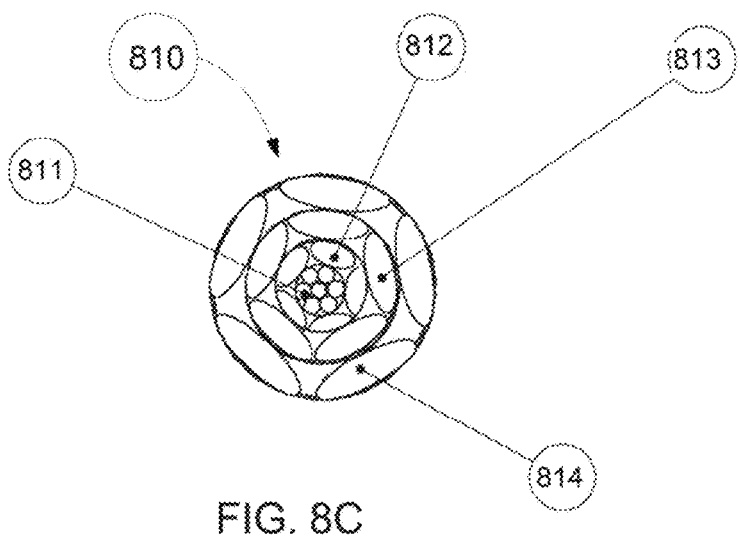
FIGS. 8B and 8C are simplified illustrations of a wire cable included in a flexible drive shaft constructed according to an example embodiment of the invention.
Figure 8B:
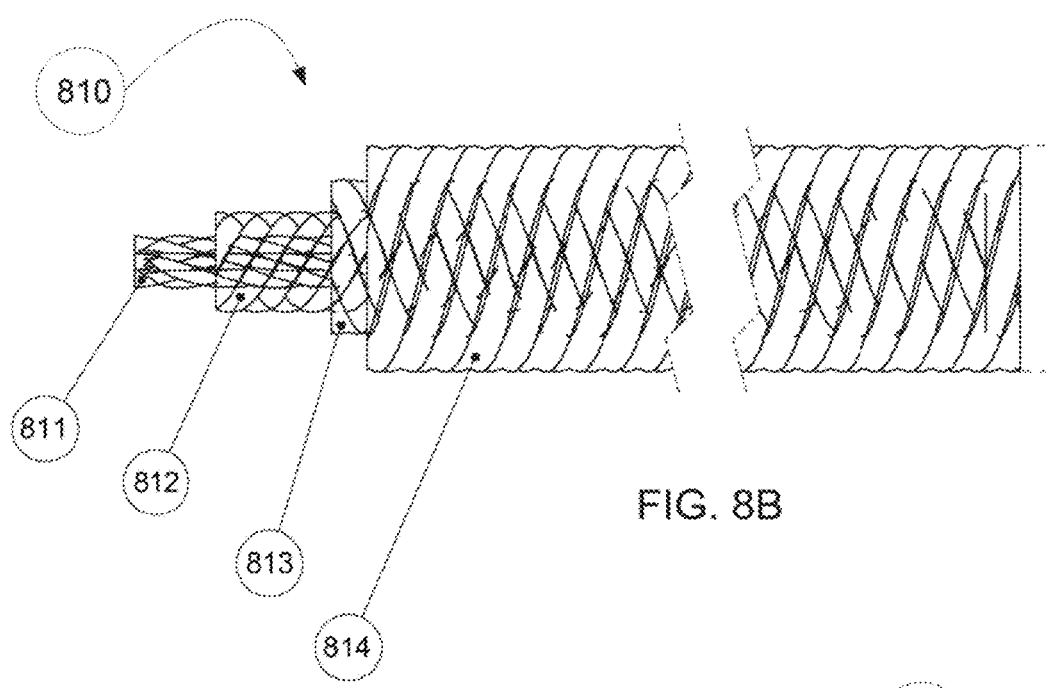
Figure 8A:
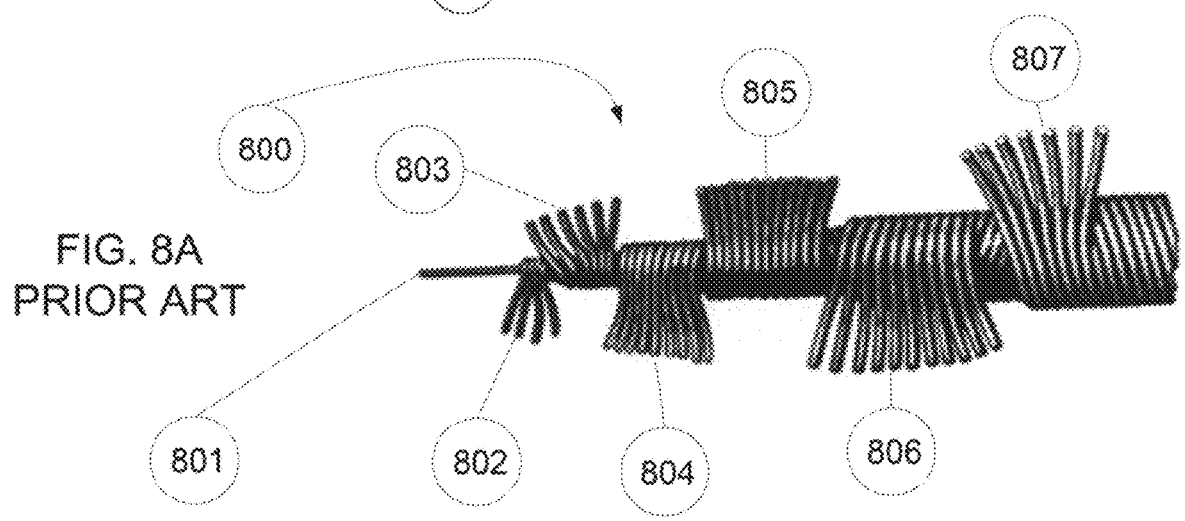
FIG. 8A is a simplified illustration of a method of manufacture of a prior art flexible drive shaft.

Reference is now made to FIG. 8A, which is a simplified illustration of a method of manufacture of a prior art flexible drive shaft 800.

A typical prior art flexible drive shaft 800 is manufactured by wrapping a mandrel 801 with a first layer of wires 802 wrapped parallel to each other in a first direction, for example clockwise, then wrapping the first layer of wires 802 by a second layer of wires 803 wrapped parallel to each other in a direction opposite to the first direction, for example counter clockwise, and continuing wrapping additional layers of wires parallel to each other, for example additional layers of wires 804, 805, 806 and 807. Finally, the mandrel 801 is removed, leaving behind a tiny hole through the first layer of wires 802. The result is a flexible drive shaft 800 with a small hole within, which may well be closed by the first layer of wires 802 closing up when the flexible drive shaft 800 is rotating.

A problem which occasionally occurs when using a flexible drive shaft is termed "helixing". Helixing is a phenomenon where a central axis of a flexible drive shaft twists in a helical or corkscrew shape upon application of sufficient torque. As the torque continues to increase, the degree of helixing may become more severe. An outer casing can limit the degree of helixing. Helixing can cause friction against the outer casing and heating up; the helixing may deform the elongated shaft body 30 which contains the flexible drive shaft, and helixing may cause premature failure of the device 10.

Reference is now made to FIGS. 8B and 8C, which are simplified illustrations of a wire cable included in a flexible drive shaft 810 constructed according to an example embodiment of the invention.

FIG. 8C depicts a cross section of the flexible drive shaft 810 of FIG. 8B.

The flexible drive shaft 810 of FIGS. 8B and 8C is constructed of a core 811 wrapped with a first layer of wires 812 wrapped parallel to each other in a first direction, for example clockwise, optionally a second layer of wires 813 wrapped parallel to each other in a direction opposite to the first direction, for example counter clockwise, and optionally additional layers of wires wrapped parallel to each other, for example an additional layer of wires 814.

The core 811 is designed to provide some stiffness with respect to bending to the flexible drive shaft. The core 811 potentially prevents helixing and/or puts off helixing to a situation of more torque than when using a flexible drive shaft which does not have a core 811.

In some embodiments, the core 811 is a multi-stranded wire core made of braided wires, rather than wires which are wrapped, or coiled, parallel to each other. Braided wire is potentially more resistant to helixing.

In some embodiments, the core 811 is a synthetic material such as nylon.

In some embodiments, the core is made from stainless steel, which is biocompatible, common in the cabling industry and affordable.

In some embodiments, the wire layers are made from stainless steel, which is biocompatible, common in the cabling industry and affordable.

The flexible drive shaft of FIGS. 8B and 8C provides high torque transmission and fatigue resistance when bent.

Experiments conducted demonstrated that transfer of high speed rotational movement with a torque sufficient for cutting hard tissue such as bone, along a curved path with small radius of curvature and large angle α can lead to failure of the flexible drive shaft, the connection between the flexible drive shaft and the cutting head or the cutting head itself. Such failure can lead to release into the body of device components, and to tissue damage, infection and the like. Another difficulty noticed was related to a short service life (i.e. time to failure) in the range of, for example, 30-120 seconds with an overall material removal volume of, for example, 8 mm$^3$-64 mm$^3$ These parameters are considered suboptimal for a surgical tool used for the medical indications described herein.

Various embodiments of the invention potentially provide functionality and predictability of a failure location (e.g. drive shaft, cutting head, cutting head-drive shaft interface, etc.).

Parameters such as tissue cutting efficacy, resistance of tissue to cutting, cutting time and force applied by the surgeon on the handle may be tested by using materials such as saw bone, wood, animal bones and human cadaver bones.

Specific designs potentially allow choosing the component which is likely to fail; for example, at the flexible shaft, such failure leaves the cutting head intact and reduces likelihood of mechanical disintegration and release of device fragments into the body.

When failure is localized, for example, to the flexible drive shaft, various solutions for maintaining device integrity following failure, such as demonstrated in various embodiments shown herein, prevent the cutting head from being released from the device following failure of the drive shaft.

Embodiments of the invention with reference to drive shaft design; to the drive shaft-cutting head interface; and to an optional addition of a mechanism for preventing the cutting head from being released from the device may increase the service life of the device 10. For example, service life of the device 10 may be increased to 600-900 seconds and may enable removal of a tissue volume of, for example, 1000 mm$^3$, while eliminating the potential problems associated with a detaching of the cutting head from the device.

Additional objects, advantages, and novel features of the present invention will become apparent to one ordinarily skilled in the art upon examination of the following examples, which are not intended to be limiting. Additionally, each of some the various embodiments and aspects of the present invention as delineated hereinabove and as claimed in the claims section below finds experimental support in the following examples.

It is expected that during the life of a patent maturing from this application many relevant cutting heads will be developed and the scope of the term cutting head is intended to include all such new technologies a priori.

The terms "comprising", "including", "having" and their conjugates mean "including but not limited to".

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although some embodiments of the invention have been described in conjunction with some specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to some embodiment of the present invention.

What is claimed is:

1. A device for cutting tissue, comprising:
   (a) an elongated shaft body defining a drive lumen,
      wherein the elongated shaft body comprises a curved distal portion having a radius of curvature that is in a range of between 4 mm and 12 mm;
   (b) a flexible drive shaft positioned within the drive lumen, wherein the flexible drive shaft comprises:
      (i) an innermost flexible core comprising a stranded, twisted, or braided cable made of a plurality of stainless-steel wires, wherein said innermost flexible core is configured for resisting helixing and for providing low bending stress; and
      (ii) a plurality of outer layers, wherein each of the plurality of outer layers comprises a layer of wires wound around the core; and
      wherein the drive shaft is configured to allow rotation at above 10,000 RPM and to transfer torque of 5 N-cm while being bent at a bending radius of less than 12 mm and an angle of less than 160 degrees between two axially separated parts of the shaft, whereby the drive shaft is configured to transfer torque while extending through the curved distal portion, and
      wherein the flexible drive shaft has an outer diameter of less than 3 mm;
   (c) a cutting head extending from a distal end of the elongated shaft body,
      wherein the cutting head is coupled to the flexible drive shaft and is rotatable by the drive shaft, and
      wherein the cutting head is configured to be rotated at above 10,000 RPM and to remove bone when a side of the cutting head contacts bone while the cutting head is rotating at above 10,000 RPM; and
   (d) a retainer for retaining the cutting head mounted on the shaft body if the cutting head becomes detached from the drive shaft or if the drive shaft breaks.

2. The device of claim 1, wherein each layer of the plurality of outer layers of the flexible drive shaft is wound in a direction opposite to the direction of an adjacent outer layer.

3. The device of claim 1, wherein the flexible drive shaft is configured to operate when temporarily or permanently bent at an angle in a range between 90 and 160 degrees.

4. The device of claim 1, wherein the flexible drive shaft is configured to support a rotational speed of up to 70,000 rpm.

5. The device of claim 1, wherein the flexible drive shaft is sufficiently designed for failure avoidance when operated at 15,000 RPM for at least 2 minutes while removing 1000 $mm^3$ of bone.

6. The device of claim 1, wherein the innermost flexible core is made of 7 stainless steel wires.

7. The device of claim 1, wherein the flexible drive shaft is permanently bent at about 135 degrees.

8. The device of claim 1, wherein the plurality of outer layers of the flexible drive shaft comprises three outer layers.

9. The device of claim 1, wherein the elongated shaft body comprises a curved distal portion, and wherein the cutting head extends from a distal end of the curved distal portion.

10. The device of claim 1, further comprising:
   a shield extending around at least a portion of the cutting head.

11. The device of claim 10, wherein the retainer is attached to the shield.

12. The device of claim 10, wherein the shield is movable.

13. The device of claim 1, wherein the retainer comprises a sleeve surrounding a portion of the cutting head.

14. The device of claim 1, wherein the cutting head comprises a groove, and wherein the retainer comprises a component configured for engaging the groove of the cutting head for retaining the cutting head within the distal portion of the elongated shaft body if the cutting head becomes detached from the drive shaft or if the drive shaft breaks.

15. The device of claim 14, wherein the component configured for engaging the groove comprises one of a tenon, a pin, or a snap.

16. The device of claim 14, wherein the component configured for engaging the groove is further configured to have low friction with the cutting head.

17. The device of claim 1, wherein the cutting head is cylindrical in shape with a circumferential surface configured for cutting of tissue.

18. The device of claim 1, wherein the cutting head comprises a groove, and wherein the retainer comprises a drive shaft sleeve crimped onto the groove for retaining the cutting head within the distal portion of the elongated shaft body if the drive shaft becomes detached from the cutting head.

19. The device of claim 1, wherein the elongated shaft body further comprises a fluid lumen.

20. The device of claim 1, wherein the radius of curvature of the curved distal portion of the elongated shaft body is 9 mm.

21. The device of claim 1, wherein the flexible drive shaft further comprises a connector positioned at a distal end of the flexible drive shaft, and wherein the cutting head is coupled to the connector of the flexible drive shaft and is rotatable by the drive shaft.

22. The device of claim 1, wherein an inner diameter of the drive lumen is 30% to 100% larger than the outer diameter of the flexible drive shaft.

* * * * *